United States Patent
Hirose et al.

(10) Patent No.: US 11,941,800 B2
(45) Date of Patent: Mar. 26, 2024

(54) OPHTHALMOLOGIC INFORMATION PROCESSING APPARATUS, OPHTHALMOLOGIC APPARATUS, OPHTHALMOLOGIC INFORMATION PROCESSING METHOD, AND RECORDING MEDIUM

(71) Applicant: TOPCON CORPORATION, Tokyo (JP)

(72) Inventors: Ryoichi Hirose, Tokyo (JP); Tatsuo Yamaguchi, Warabi (JP); Suguru Miyagawa, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 698 days.

(21) Appl. No.: 17/099,828

(22) Filed: Nov. 17, 2020

(65) Prior Publication Data

US 2021/0073988 A1 Mar. 11, 2021

Related U.S. Application Data

(63) Continuation of application No. PCT/JP2019/050608, filed on Dec. 24, 2019.

(30) Foreign Application Priority Data

Feb. 27, 2019 (JP) ................. 2019-034433

(51) Int. Cl.
*G06K 9/00* (2022.01)
*A61B 3/00* (2006.01)
(Continued)

(52) U.S. Cl.
CPC .......... *G06T 7/0012* (2013.01); *A61B 3/0025* (2013.01); *A61B 3/0041* (2013.01);
(Continued)

(58) Field of Classification Search
None
See application file for complete search history.

(56) References Cited

U.S. PATENT DOCUMENTS

| 5,815,242 A | 9/1998 | Anderson et al. |
| 2003/0103191 A1 | 6/2003 | Staurenghi et al. |

(Continued)

FOREIGN PATENT DOCUMENTS

| EP | 1308124 A2 | 5/2003 |
| JP | 2017-221742 A | 12/2017 |

(Continued)

OTHER PUBLICATIONS

International Search Report and Written Opinion dated Mar. 3, 2020 for PCT/JP2019/050608 filed on Dec. 24, 2019, 8 pages including English Translation of the International Search Report.

(Continued)

*Primary Examiner* — Soo Jin Park
(74) *Attorney, Agent, or Firm* — XSENSUS LLP

(57) ABSTRACT

An ophthalmologic information processing apparatus analyzes an image of a subject's eye formed by arranging a plurality of A-scan images acquired by performing OCT scan on inside the subject's eye with measurement light deflected around a scan center position. The ophthalmologic information processing apparatus includes a correcting unit, a region specifying unit, and a direction specifying unit. The correcting unit is configured to transform a pixel position in the image into a transformation position along a traveling direction of the measurement light passing through the scan center position. The region specifying unit is configured to specify a predetermined layer region by analyzing the image in which the pixel position has been transformed by the correcting unit. The direction specifying unit is configured to specify a normal direction of the layer region specified by the region specifying unit.

18 Claims, 15 Drawing Sheets

(51) Int. Cl.
  *A61B 3/10* (2006.01)
  *A61B 3/12* (2006.01)
  *G06T 3/20* (2006.01)
  *G06T 7/00* (2017.01)

(52) U.S. Cl.
  CPC ............ *A61B 3/102* (2013.01); *A61B 3/1225* (2013.01); *G06T 3/20* (2013.01); *G06T 2207/10101* (2013.01); *G06T 2207/30041* (2013.01)

(56) References Cited

U.S. PATENT DOCUMENTS

| | | |
|---|---|---|
| 2012/0288175 A1 | 11/2012 | Iwase et al. |
| 2017/0273557 A1* | 9/2017 | Nakazawa ............ A61B 3/1225 |
| 2018/0289257 A1 | 10/2018 | Ikegami |
| 2020/0138283 A1 | 5/2020 | Yamaguchi et al. |

FOREIGN PATENT DOCUMENTS

| | | |
|---|---|---|
| JP | 2018-175258 A | 11/2018 |
| JP | 2019-13362 A | 1/2019 |
| WO | 2015/165989 A2 | 11/2015 |

OTHER PUBLICATIONS

Extended European Search Report dated Nov. 23, 2022 in corresponding European Patent Application No. 19916685.1, 10 pages.
Cabrera Debuc, Delia, "A Review of Algorithms for Segmentation of Retinal Image Data Using Optical Coherence Tomography", Image Segmentation, InTech, XP055147619, Apr. 19, 2011, 41 pages.

* cited by examiner

OPHTHALMOLOGIC INFORMATION PROCESSING APPARATUS, OPHTHALMOLOGIC APPARATUS, OPHTHALMOLOGIC INFORMATION PROCESSING METHOD, AND RECORDING MEDIUM

CROSS-REFERENCE TO RELATED APPLICATIONS

The present application is a continuation application of International Patent Application No. PCT/JP2019/050608, filed Dec. 24, 2019, which claims priority to Japanese Patent Application No. 2019-034433, filed Feb. 27, 2019. The contents of these applications are incorporated herein by reference in their entirety.

FIELD

The disclosure relates to an ophthalmologic information processing apparatus, an ophthalmologic apparatus, an ophthalmologic information processing method, and a recording medium.

BACKGROUND

There is a demand for ophthalmologic apparatuses capable of easily observing or imaging a fundus of a subject's eye with a wide field of view for screening or treating eye diseases. Optical coherence tomography and Scanning Laser Ophthalmoscope (hereinafter, SLO) are known as such ophthalmologic apparatuses. SLO is an apparatus configured to form an image of the fundus by scanning the fundus with light to detect returning light of the light with a light receiving device.

Various ophthalmologic apparatuses for observing the fundus with such a wide field of view have been proposed. For example, in European Unexamined Patent Application Publication No. 1308124, a method of acquiring a wide-angle image of the subject's eye by bringing a contact lens included in the objective lens system into contact with the cornea of the subject's eye is disclosed. Further, for example, in U.S. Pat. No. 5,815,242, a method of providing an anterior segment imaging system in the ophthalmologic apparatus for acquiring a wide-angle image of the subject's eye using an ellipsoidal mirror and imaging an anterior segment of the subject's eye using the anterior segment imaging system is disclosed.

SUMMARY

One aspect of some embodiments is an ophthalmologic information processing apparatus for analyzing an image of a subject's eye formed by arranging a plurality of A-scan images acquired by performing OCT scan on inside the subject's eye with measurement light deflected around a scan center position. The ophthalmologic information processing apparatus includes: a correcting unit configured to transform a pixel position in the image into a transformation position along a traveling direction of the measurement light passing through the scan center position; a region specifying unit configured to specify a predetermined layer region by analyzing the image in which the pixel position has been transformed by the correcting unit, and a direction specifying unit configured to specify a normal direction of the layer region specified by the region specifying unit.

Another aspect of some embodiments is an ophthalmologic apparatus including: an OCT unit configured to acquire a tomographic image of the subject's eye using optical coherence tomography: and the ophthalmologic information processing apparatus described above.

Yet another aspect of some embodiments is an ophthalmologic information processing method for analyzing an image of a subject's eye formed by arranging a plurality of A-scan images acquired by performing OCT scan on inside the subject's eye with measurement light deflected around a scan center position. The ophthalmologic information processing method includes: a correcting step of transforming a pixel position in the image into a transformation position along a traveling direction of the measurement light passing through the scan center position; a region specifying step of specifying a predetermined layer region by analyzing the image in which the pixel position has been transformed in the correcting step, and a direction specifying step of specifying a normal direction of the layer region specified in the region specifying step.

Yet another aspect of some embodiments is a non-transitory computer readable recording medium storing a program of causing a computer to execute each step of the ophthalmologic information processing method described above.

DETAILED DESCRIPTION

Figure 1:
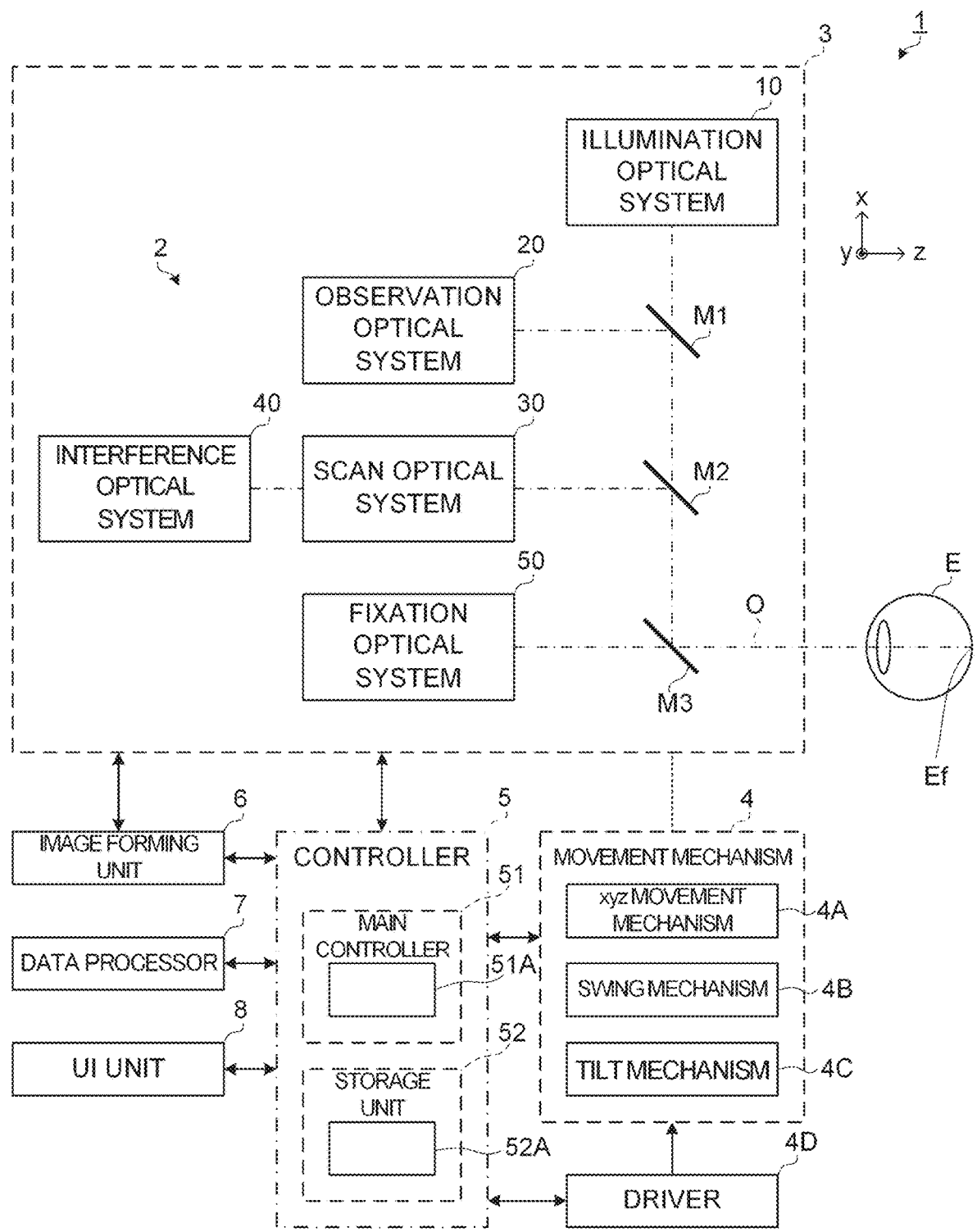
FIG. 1 is a schematic diagram illustrating an example of a configuration of an ophthalmologic apparatus according to embodiments.

As the tomographic images of the subject's eye, which are acquired using optical coherence tomography, become wider, the doctor or the like can make diagnoses more accurately. On the other hand, an incident angle of measurement light with respect to the fundus in the central part of the fundus differs from an incident angle of the measurement light with respect to the fundus in the peripheral part of the fundus. Therefore, it is desirable to evaluate the measurement result using the measurement light according to the incident position of the measurement light. For example, in case that a thickness in the depth direction (cross-sectional direction) in the central part of the fundus is different from a thickness in the depth direction in the peripheral part of the fundus, it is necessary to determine whether it is due to the shape of the fundus or depending on the incident angle of the measurement light.

According to some embodiments according to the present invention, a new technique for accurately grasping a morphology of the fundus or the like of the subject's eye can be provided.

Referring now to the drawings, exemplary embodiments of an ophthalmologic information processing apparatus, an ophthalmologic apparatus, an ophthalmologic information processing method, and a recording medium according to the present invention are described below. Any of the contents of the documents cited in the present specification and arbitrary known techniques may be applied to the embodiments below.

An ophthalmologic information processing apparatus according to embodiments analyzes an image of a subject's eye obtained by arranging a plurality of A-scan images acquired by performing OCT (Optical Coherence Tomography) scan on inside the subject's eye with measurement light deflected around a scan center position. The ophthalmologic information processing apparatus transforms a pixel position in the obtained image into a transformation position along a traveling direction of the measurement light passing through the scan center position, so that the shape of the fundus etc. drawn on the image to be analyzed becomes a real shape. Further, the ophthalmologic information processing apparatus specifies a predetermined layer region by analyzing the image, in which the pixel position has been transformed described above, and specifies a normal direction of the specified layer region.

In some embodiments, the ophthalmologic information processing apparatus obtains a distance in the normal direction in the specified layer region. This allows to correctly acquire a thickness of the layer region in the peripheral part of the fundus and a thickness of the layer region when the shape of the fundus is deformed, similarly to the central part of the fundus.

In some embodiments, the ophthalmologic information processing apparatus displays the image, in which the pixel position has been transformed as described above, in the normal direction. This allows to correctly grasp not only the morphology of the peripheral part of the fundus but also the morphology etc. of the deformed fundus.

An ophthalmologic information processing method according to the embodiments includes one or more steps for realizing the processing executed by a processor (computer) in the ophthalmologic information processing apparatus according to the embodiments. A program according to the embodiments causes the processor to execute each step of the ophthalmologic information processing method according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

In this specification, an image acquired using OCT may be collectively referred to as an "OCT image". Further, a measuring action for forming an OCT image is sometimes referred to as an OCT measurement. And, a scan for performing OCT measurement is sometimes referred to as an OCT scan.

Hereinafter, the case where the ophthalmologic apparatus according to the embodiments has the function of the ophthalmologic information processing apparatus according to the embodiments will be described. However, the ophthalmologic information processing apparatus according to the embodiments may be configured to acquire tomographic images from an external ophthalmologic apparatus.

The ophthalmologic apparatus according to the embodiments can scan an anterior segment or a posterior segment of a subject's eye with light beam to acquire a distribution of predetermined data (for example, an image, a layer thickness distribution, a lesion distribution). Examples of the ophthalmologic apparatus include optical coherence tomography, SLO, and the like. Hereinafter, a case where the ophthalmologic apparatus has a function of an optical coherence tomography will be described.

In some embodiments, the ophthalmologic apparatus includes a swing mechanism configured to move an optical system in a horizontal direction with reference to the subject's eye, and scans the posterior segment at a wide angle by moving the optical system in the horizontal direction. In some embodiments, the ophthalmologic apparatus includes a tilt mechanism configured to move the optical system in a vertical direction with reference to the subject's eye, and scans the posterior segment at a wide angle by moving the optical system in the vertical direction. In some embodiments, the ophthalmologic apparatus includes the swing mechanism and the tilt mechanism. In some embodiments, the ophthalmologic apparatus includes a fixation optical system configured to project fixation light flux onto the fundus of the subject's eye, and scans the posterior segment at a wide angle by changing a projected position of the fixation light flux on the fundus. An internal fixation optical system or an external fixation optical system can be used for projecting the fixation light flux.

Hereinafter, the case where the ophthalmologic apparatus according to the embodiments includes the swing mechanism, the tilt mechanism, and the fixation optical system will be described. However, the ophthalmologic apparatus according to the embodiments may have a configuration in which at least one of the swing mechanism, the tilt mechanism, and the fixation optical system is omitted.

In the following description, unless otherwise stated, the left-right direction viewed from the subject is regarded as an x direction, the up-down direction is regarded as a y direction, and the front-back direction (depth direction) is regarded as a z direction. The x direction, the y direction, and the z direction define a three-dimensional orthogonal coordinate system.

<Configuration>

FIG. 1 shows a schematic configuration of an ophthalmologic apparatus according to embodiments. The ophthalmologic apparatus 1 according to the embodiments scans the fundus Ef of the subject's eye E with light to acquire data, and obtains an image of the fundus Ef based on the acquired data. In FIG. 1, a tomographic image of the fundus Ef, a three-dimensional image of the fundus Ef, a front image of the fundus Ef, or the like can be obtained.

The ophthalmologic apparatus 1 includes an optical system 2, a housing unit 3 configured to house the optical system 2, a movement mechanism 4, a controller 5, an image forming unit 6, a data processor 7, and a user interface (UI) unit 8. The ophthalmologic apparatus 1 may include a driver 4D that drives the movement mechanism 4 under the control of the controller 5.

<Movement Mechanism>

The movement mechanism 4 moves the optical system 2 (housing unit 3). The movement mechanism 4 includes an xyz movement mechanism 4A, a swing mechanism 4B, and a tilt mechanism 4C. The xyz movement mechanism 4A moves the optical system 2 in the x direction, the y direction, and the z direction. The swing mechanism 4B swings (rotates) the optical system 2 in the horizontal direction with reference to a predetermined position (for example, pupil position) of the subject's eye E. Specifically, the swing mechanism 4B moves the optical system 2 in the horizontal direction along an arc-like trajectory. The swing mechanism 4B swings the optical system 2 within a predetermined movement angle range. The tilt mechanism 4C swings (rotates) the optical system 2 in the vertical direction with reference to a predetermined position (for example, pupil position) of the subject's eye E. Specifically, the tilt mechanism 4C moves the optical system 2 in the vertical direction along an arc-like trajectory. The tilt mechanism 4C swings the optical system 2 within a predetermined movement angle range. The center of swing motion is not limited to the pupil position. The center of swing motion may be a position displaced from the pupil position within a range that does not interfere with scans on the posterior segment. A position within such a range is referred to as a "near position of the pupil position". It should be noted that the displacement of the near position with respect to the pupil position may be a displacement in an arbitrary direction in the xyz space. Hereinafter, unless otherwise stated, the "pupil position" means the "pupil position or near position of the pupil position".

The xyz movement mechanism 4A is used, for example, in a position matching (alignment) of the optical system 2 with respect to the subject's eye E and a tracking. Here, the tracking is to move the optical system 2 according to the movement of the subject's eye E. To perform tracking, alignment and focusing are performed in advance. The tracking is performed by moving the optical system 2 in real time according to the position and orientation of the subject's eye E based on the image obtained by imaging (movie shooting) the subject's eye E, thereby maintaining a suitable positional relationship in which alignment and focusing are adjusted.

The swing mechanism 4B and the tilt mechanism 4C are used for wide-range scan for the subject's eye E (fundus Ef) and imaging of the peripheral part of the fundus Ef. The swing mechanism 4B and the tilt mechanism 4C three-dimensionally swings, for example, the optical system 2 around the pupil position within a predetermined movement angle range.

The movement mechanism 4 of this sort includes, for example, one or more holding members that hold the optical system 2 and one or more guide arms provided so as to be capable of moving to arbitrary positions within the above movement angle range. The movement mechanism 4 slides along the guide arm. It should be noted that the dimension of the rotating direction is not limited to three dimensions. The dimension of the rotating direction may be one dimension or two dimensions, for example.

The driver 4D operates, for example, under the control of the controller 5. In this case, the driver 4D includes an actuator (not shown) that generates a driving force for rotating the optical system 2. The actuator generates the driving force corresponding to a control signal from the controller 5. This driving force is transmitted by a transmission mechanism (not shown). Thereby, the holding member can be moved along the guide arm. Using such control, the optical system 2 is rotated in the direction corresponding to the control signal by the angle corresponding to the control signal. In this case, a position of the optical system 2 is specified by the control content of the driver 4D by the controller 5. The specified position information (movement information) is used by the controller 5, the image forming unit 6, the data processor 7, or the like, for example.

Further, the movement mechanism 4 may not include the actuator. In this case, the optical system 2 is rotated manually. The position of the optical system 2 is detected by an encoder or a position sensor. Thereby, the acquired position information is used by the controller 5, the image forming unit 6, the data processor 7, and the like, for example.

In some embodiments, the movement mechanism 4 moves the optical system 2 by moving the housing unit 3. In some embodiments, the movement mechanism 4 moves a part of the optical system 2 alone.

<Optical System>

The optical system 2 includes an optical member and a mechanism for optically acquiring data of the fundus Ef. The optical system 2 includes an illumination optical system 10, an observation optical system 20, a scan optical system 30, an interference optical system 40, and a fixation optical system 50. In some embodiments, the optical system 2 includes at least one of an alignment system for performing alignment of the optical system 2 with respect to the subject's eye E and a focus system for performing focus of the optical system 2 with respect to the subject's eye E.

The optical system 2 includes an optical element as an optical path coupling/separating member for separating the optical path of the optical system described above or coupling with another optical system. In FIG. 1, for example, beam splitters M1 to M3 are provided as the optical path coupling/separating members.

The beam splitter M1 couples an optical path of the illumination optical system 10 and an optical path of the observation optical system 20, or separates the optical path of the observation optical system 20 from an optical path of light transmitted through the beam splitter M2.

The beam splitter M1 has a characteristic of transmitting light from the illumination optical system 10, and of reflecting light transmitted through the beam splitter M2 toward the observation optical system 20. It is preferred that the beam splitter M1 couples the illumination optical system 10 and the observation optical system 20 so that the optical axis of the illumination optical system 10 is substantially coaxial with the optical axis of the observation optical system 20.

The beam splitter M2 couples an optical path of the scan optical system 30 (or the interference optical system 40) and the optical path of the illumination optical system 10 (or the observation optical system 20), or separates the optical path of the scan optical system 30 (or the interference optical system 40) and the optical path of the illumination optical system 10 (or the observation optical system 20) from an optical path of light reflected by the beam splitter M3. The beam splitter M2 has a characteristic of transmitting light from the beam splitter M1, of reflecting light from the scan optical system 30 toward the beam splitter M3, of reflecting returning light, which returns from the subject's eye E, of light from the scan optical system 30 toward to the scan optical system 30, and of transmitting returning light, which returns from the subject's eye E, of light from the illumination optical system 10. It is preferred that the beam splitter M2 couples the scan optical system 30 (or the interference optical system 40) and the illumination optical system 10 (or observation optical system 20) so that the optical axis of the scan optical system 30 is substantially coaxial with the optical axis of the illumination optical system 10.

The beam splitter M3 couples an optical path of the fixation optical system 50 and the optical paths of the other optical systems. The beam splitter M3 has a characteristic of transmitting light from the fixation optical system 50, and of reflecting light from the other optical systems (the illumination optical system 10 and the interference optical system 40) or returning light thereof. It is preferred that the beam splitter M3 couples the fixation optical system 50 and the other optical systems so that the optical axis of the fixation optical system 50 is substantially coaxial with the optical axes of the other optical systems.

In FIG. 1, an objective lens (not illustrated) is located between the beam splitter M3 and the subject's eye E.

(Illumination Optical System)

The illumination optical system 10 illuminates an anterior segment of the subject's eye E. The illumination optical system 10 includes an illumination light source, a lens, and the like.

(Observation Optical System)

The observation optical system 20 is used for observing the anterior segment of the subject's eye E illuminated by the illumination optical system 10. The observation optical system 20 includes at least one of an eyepiece and an imaging element. The eyepiece is used for observing the subject's eye E with the naked eye(s). The imaging element is used for acquiring a front image of the subject's eye E.

Illumination light from the illumination optical system 10 is transmitted through the beam splitters M1, M2, is reflected by the beam splitter M3, and passes through the objective lens (not shown) to illuminate the anterior segment of the subject's eye E. Returning light of the illumination light from the subject's eye E travels on the same path in the opposite direction, is reflected by the beam splitter M1, and enters the observation optical system 20. The returning light entered the observation optical system 20 is focused on an imaging surface of the imaging element, for example. The controller 5 that has received a signal from the imaging element controls the UI unit 8 to display the image acquired using the imaging element on a display device (not shown).

(Scan Optical System)

The scan optical system 30 deflects measurement light output from the interference optical system 40 under the control of the controller 5. For example, the scan optical system 30 deflects light within a two-dimensional deflection angle range. It should be noted that the dimension of the deflecting direction is not limited to two dimensions. The dimension of the deflecting direction may be one dimension, for example.

The scan optical system 30 includes an optical scanner. A uniaxial deflecting member or a biaxial deflecting member is used as the optical scanner. Deflecting directions of the biaxial deflecting member are orthogonal to each other. Examples of the deflecting member include a galvano mirror, a polygon mirror, a rotating mirror, a dove prism, a double dove prism, a rotation prism, and a MEMS mirror scanner. When the biaxial deflecting member is used, a deflecting member for high speed scanning (for example, the polygon mirror) and a deflecting member for low speed scanning (for example, the galvano mirror) can be combined. The scan optical system 30 may further include an optical element for projecting the deflected light onto the fundus Ef.

The optical scanner is disposed at a position optically substantially conjugate with the pupil of the subject's eye E or near the position. This allows to scan inside of the subject's eye E with the measurement light deflected around a scan center position, with the pupil (or the vicinity thereof) of the subject's eye E as the scan center position.

(Interference Optical System)

The interference optical system 40 is configured to split light from a light source into measurement light and reference light, to project the measurement light onto the subject's eye E (fundus Ef), and to guide interference light, which is obtained by superimposing returning light of the measurement light from the subject's eye E and the reference light, to a detector. For the interference optical system 40, for example, a swept source type or a spectral domain type OCT (Optical Coherence Tomography) is applied.

When the swept source type OCT is applied, the interference optical system 40 includes an OCT light source. The OCT light source is a wavelength sweeping type (i.e., a wavelength scanning type) light source capable of sweeping (scanning) the wavelengths of emitted light. For example, a laser light source, which includes a resonator and emits light having a predetermined center wavelength, is used as the wavelength sweeping type light source. The wavelength swept type light source temporally changes the output wavelength in the near infrared wavelength band which cannot be visually recognized by the human eye.

Light output from the OCT light source may be, for example, near infrared light having a center wavelength of about 1040 nm to 1060 nm (for example, 1050 nm) and a wavelength width of about 50 nm. In the embodiments, the swept source type is particularly described. However, when the spectral domain type OCT is applied, a light output device, such as a super luminescent diode (SLD), an LED, a semiconductor optical amplifier (SOA), or the like is used as the light source. Generally, the configuration of the OCT light source is selected as appropriate according to the type of optical coherence tomography.

Light output from the OCT light source is guided through an optical fiber to a fiber coupler, and is split into the measurement light and the reference light. The measurement light is guided through an optical fiber, is emitted from the end of the fiber, and is collimated into a parallel light flux by a collimator lens. The end of this optical fiber is located at the fundus conjugate position or near the position. The fundus conjugate position is optically conjugate with the fundus Ef of the subject's eye E. The measurement light is deflected by the scan optical system 30, is reflected by the beam splitter M2, and is reflected by the beam splitter M3 toward the subject's eye E. The measurement light irradiated onto the fundus Ef is scattered and reflected at, for example, the measurement site(s) such as the fundus Ef. The scattered and reflected light may be sometimes referred to as returning light of the measurement light. The returning light of the measurement light travels through the same path in the opposite direction, and is thereby guided to the fiber coupler described above.

On the other hand, the reference light is guided through an optical fiber, is reflected by a reference mirror movable along the optical path of the reference light. The reflected light is again guided to the fiber coupler described above. It should be noted that a polarization controller (polarization adjuster), an optical element for dispersion compensation (pair prism, etc.), an optical element for polarization correction (wavelength plate, etc.), or an optical attenuator (attenuator) may be provided on the optical path of the reference light. The optical attenuator adjusts the amount of the reference light passing through the optical fiber under the control of the controller 5. The polarization controller applies external stress to the looped optical fiber, for example, to thereby adjust the polarized wave (polarization) condition of the reference light guided through the optical fiber.

An optical path length changing unit is provided on at least one of the optical path of the reference light and the optical path of the measurement light. The optical path length changing unit relatively changes the optical path length of the measurement light with respect to the optical path length of the reference light. This change in the optical path length is used for correcting the optical path length according to the axial length, adjusting the interference state, or the like, Such an optical path length changing unit includes, for example, a corner cube and a mechanism that moves the corner cube along the optical path of the incident light in response to an instruction from the controller 5.

The returning light of the measurement light and the reference light reflected by the reference mirror enter the fiber coupler described above. The fiber coupler superposes the returning light of the measurement light on the reference light. Interference light thus generated is guided to a detector through an optical fiber. At this time, a pair of interference light is generated by another fiber coupler. The another fiber coupler generates the pair of interference light by branching the interference light at a predetermined branching ratio (for example, 1:1). The pair of interference light is detected by the detector (balanced photodiode). It should be noted that the detector (spectrometer) detects the interference light generated by the fiber coupler by decomposing it into a plurality of wavelength components in the case of spectral domain OCT.

The detector sends a detection result (detection signal) of the pair of interference light to a data acquisition system (DAQ) (not shown). The DAQ is fed with a clock from the OCT light source. This clock is generated in synchronization with the output timing of each wavelength swept within a predetermined wavelength range by the wavelength swept type light source. The DAQ performs sampling of the detection signal based on the clock. The sampling result is sent to the image forming unit 6 for forming an OCT image.

(Fixation Optical System)

The fixation optical system 50 projects fixation light flux onto the fundus Ef of the subject's eye E. The fixation optical system 50 is configured to be able to change the projected position of the fixation light flux on the fundus Ef of the subject's eye E under the control of the controller 5.

The fixation optical system 50 of this sort includes a display device such as a liquid crystal display that displays visual target patterns in response to an instruction from the controller 5. The display device can change the projected position of the fixation light flux on the fundus Ef by changing the display position of the visual target pattern. In some embodiments, the fixation optical system 50 includes a plurality of fixation light sources, and selectively turns on the plurality of fixation light sources in response to an instruction from the controller 5. In this case, the fixation optical system 50 can change the projected position of the fixation light flux on the fundus Ef by changing the fixation light source to be turned on among the plurality of fixation light sources. Each of the plurality of fixation light sources is a visible light source that outputs visible light. In some embodiments, the ophthalmologic apparatus 1 may be provided with a plurality of external fixation light sources. The plurality of external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. For example, the movable fixation target can be generated by selectively turning on the plurality of external fixation light sources. In some embodiments, the movable fixation target can be generated using one or more movable external fixation light sources.

As described above, the optical system 2 may be provided with an alignment system and/or a focus system. The alignment system or the focus system includes an optical system for projecting an index (alignment index, focusing index) onto the subject's eye E and an optical system for detecting returning light thereof, as in the conventional configuration. In addition, two or more imaging devices that image the anterior segment of the subject's eye E can be provided. In this case, alignment is performed by analyzing two or more anterior segment images acquired substantially simultaneously by these imaging devices (for example, using trigonometry).

<Regarding Scan>

In the optical system 2, for example, the measurement light generated from the OCT light source in the interference optical system 40 is deflected by the scan optical system 30 and is imaged as spot light on the fundus Ef through the pupil of the subject's eye E. The returning light is light that returns from a projected position of the spot light (or in the vicinity of the position) to the optical system 2. The returning light is guided through the fiber coupler as described above, and is superposed with the reference light. This interference light between the returning light of the measurement light and the reference light is detected by the detector. The detector generates an electrical signal (light reception signal) by photoelectric conversion. In addition, the projected position of the spot light may be described as a spot position.

This series of processes corresponds to measurement of one point of the fundus Ef. The scan optical system 30 moves the spot position within the predetermined deflection angle range. That is, the scan within the predetermined deflection angle range is realized by the scan optical system 30. Further, the movement mechanism 4 rotates the optical system 2 within the predetermined movement angle range. That is, the movement mechanism 4 moves a scan area (single scan area) corresponding to the deflection angle range of the scan optical system 30. By combining these, a wide range of the fundus Ef can be measured while moving the single scan area.

Figure 2:
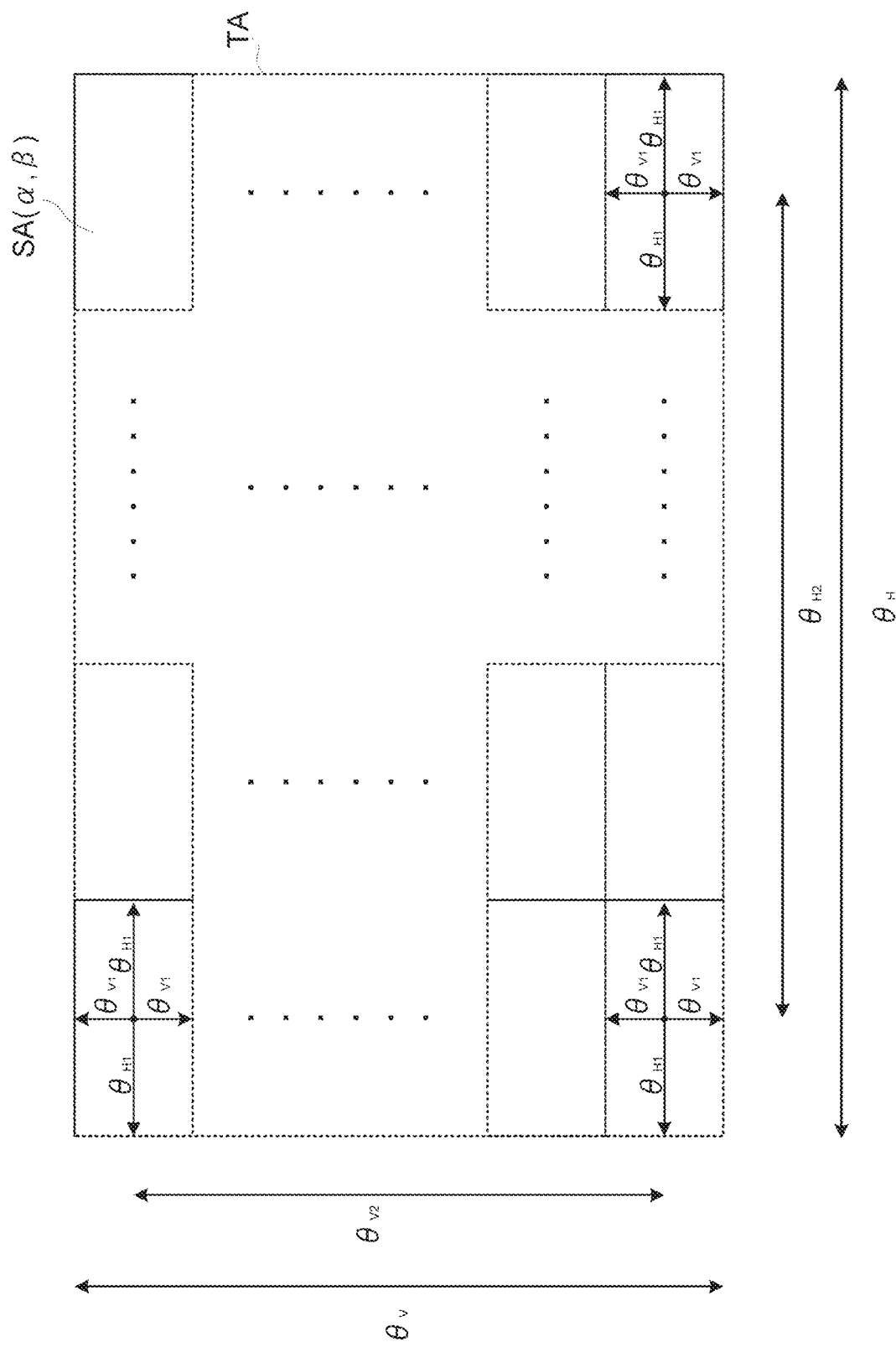
FIG. 2 is a schematic diagram for explaining processing performed by the ophthalmologic apparatus according to the embodiments.

FIG. 2 shows a diagram describing the scan operation in the ophthalmologic apparatus 1 according to the embodiments.

As shown in FIG. 2, an entire scan area TA includes one or more sub-scan areas SA (α, β). The range in the horizontal direction (for example, the x direction) of the entire scan area TA is defined as "$\theta_H$". The range in the vertical direction (for example, the y direction) of the entire scan areas TA is defined as "θv". The entire scan area TA is divided into a plurality of sub-scan areas SA (α, β) arranged vertically and horizontally. Here, α=1, 2, . . . , J and β=1, 2, . . . , K. J and K are each an integer of 1 or more, and at least one of J and K is an integer of 2 or more. In addition, it is not necessary that all of the plurality of sub-scan areas SA (α, β) have the same size. It is not necessary that all of the plurality of sub-scan areas SA (α, β) have the same shape.

Each sub-scan area SA (α, β) corresponds to the single scan area. A part of the sub-scan area SA (α, β) and a part of the sub-scan area SA (α+1, β) may overlap. A part of the sub-scan area SA (α, β) and a part of the sub-scan area SA (α, β+1) may overlap.

In the embodiments, by scanning a plurality of sub-scan areas SA (α, β) sequentially, scanning of the entire scan area TA is realized. By controlling the scan optical system 30, scanning of each sub-scan area SA (α, β) is performed. By controlling the movement mechanism 4, the sub-scan area SA (α, β) to be scanned is changed.

A scan of each sub-scan area SA (α, β) will be described. For example, the scan optical system 30 deflects the measurement light from the interference optical system 40 within the predetermined deflection angle range. The range in the horizontal direction of this deflection angle range is defined as "$2\cdot\theta_{H1}$". The range in the vertical direction of this deflection angle range is defined as "$2\cdot\theta_{V1}$". That is, the scan optical system 30 can move the spot position by "$\theta_{H1}$" in the left-right direction with reference to a center of the deflection (for example, the position on the optical axis of the scan optical system 30). The scan optical system 30 can move the spot position by "$\theta_{V1}$" in the up-down direction with reference to the center of the deflection. It should be noted that the deflection angle and the distance (chord length) in the xy plane correspond to each other. Thereby, they can be regarded as the same.

The sub-scan area SA (α, β) is switched by rotating the optical system 2 within the predetermined movement angle range around the pupil position using the movement mechanism 4. The range in the horizontal direction of this movement angle range is defined as "$\theta_{H2}$". The range in the vertical direction of this movement angle range is defined as "$\theta_{V2}$". That is, the movement mechanism 4 can swing the optical system 2 by "$\theta_{H2}$" in the horizontal direction. The movement mechanism 4 can swing the optical system 2 by "$\theta_{V2}$" in vertical direction.

According to the scan optical system 30 and the movement mechanism 4 of these sorts, when the plurality of sub-scan areas SA (α, β) are arranged without overlapping or gaps, the movement range of the spot position in the horizontal direction is $\theta_H = \theta_{H2} + 2\times\theta_{H1}$, and the movement range of the spot position in the vertical direction is $\theta_V = \theta_{V2} + 2\times\theta_{V1}$. An area where the range in the horizontal direction is $\theta_H$ and the range in the vertical direction is $\theta_V$ corresponds to the entire scan area TA. It should be noted that when an overlap or a gap is provided, the entire scan area TA is determined according to the overlap width and the gap interval.

In one example, $\theta_{H1}$=60 degrees, $\theta_{H2}$=40 degrees, $\theta_{V1}$=40 degrees, and $\theta_{V2}$=40 degrees are set. This allows to scan within a range of 160 degrees in the horizontal direction and 120 degrees in the vertical direction. It should be noted that $\theta_{H1}$, $\theta_{H2}$, $\theta_{V1}$, and $\theta_{V2}$ are determined in consideration of arbitrary factors such as cost and working distance.

<Controller>

The controller 5 controls each part of the apparatus. The controller 5 includes a processor and a storage device (storage circuit). The storage device stores in advance computer programs for controlling the ophthalmologic apparatus 1. Examples of the computer program include a program for controlling light source, a program for controlling scan, a program for controlling movement mechanism, a program for controlling image forming, a program for controlling data processing, and a program for controlling user interface. The processor operates under these computer programs, and thereby the controller 5 performs the control operation.

The controller 5 includes a main controller 51 and a storage unit 52.

(Main Controller)

The main controller 51 includes a processor and controls each part of the ophthalmologic apparatus 1. For example, the main controller 51 controls the optical system 2, the movement mechanism 4 (driver 4D), the image forming unit 6, the data processor 7, the UI unit 8, and the like.

Examples of control for the optical system 2 include control for the focusing driver that moves the focusing lens (not shown), control for the imaging element such as an image sensor, control for the optical scanner, control for the optical path length changing unit, control for the optical attenuator, control for the polarization controller, and control for the fixation optical system 50 (display device). In some embodiments, the focusing lens is arranged between the scan optical system 30 and the beam splitter M2. In some embodiments, the focusing lens is included in the observation optical system 20.

Examples of control for the movement mechanism 4 include control for the driver that drives the xyz movement mechanism 4A, control for the driver that drives the swing mechanism 4B, and control for the driver that drives the tilt mechanism 4C.

In the case of manual alignment, a user operates the UI unit 8 described later to relatively move the optical system and subject's eye E so as to cancel the displacement of the subject's eye E with respect to the optical system. For example, the main controller 51 controls the xyz movement mechanism 4A to relatively move the optical system 2 and the subject's eye E by outputting a control signal corresponding to the operation content with respect to the UI unit 8 to the xyz movement mechanism 4A (driver 4D).

In the case of automatic alignment, the main controller 51 controls the xyz movement mechanism 4A to relatively move the optical system and the subject's eye E so as to cancel the displacement of the subject's eye E with respect to the optical system. For example, the xyz movement mechanism 4A is controlled so as to cancel a displacement between (a reference position of) the image of the subject's eye E acquired using imaging optical system (not shown) and a reference position of the optical system. In some embodiments, the main controller 51 controls the xyz movement mechanism 4A to relatively move the optical system 2 and the subject's eye E by outputting a control signal to the xyz movement mechanism 4A (driver 4D) so that the measurement optical axis O of the optical system 2 substantially coincides with the axis of the subject's eye E and the distance of the optical system with respect to the subject's eye E is a predetermined working distance. Here, the working distance is a preset value which is called a working distance of the objective lens (not shown), and it means the distance between the subject's eye E and the optical system 2 when measuring (imaging) using the optical system.

Further, by controlling the scan optical system 30 and the movement mechanism 4 in liaison with each other, scan as illustrated in FIG. 2 can be realized. For example, the storage device (storage unit 52) in the main controller 51 stores a previously defined deflection pattern for deflecting the measurement light and a previously defined movement pattern for moving the optical system 2, in advance. The deflection pattern and/or the movement pattern may be set by default or may be set by the user. In addition, a plurality of deflection patterns and a plurality of movement patterns may be applied in any combination. The selection of the pattern is performed by, for example, the user or the main controller 51.

The main controller 51 executes the control (scan control) for the scan optical system 30 based on the deflection pattern and the control (movement control) for the movement mechanism 4 based on the movement pattern in liaison with each other. For example, the main controller 51 executes the scan control and the movement control alternately. Here, a single scan control corresponds to scanning a single scan area (one sub-scan area) A single movement control corresponds to switching sub-scan areas. As another example, the main controller 51 can execute the scan control and the movement control in parallel in at least some phases of scanning for the entire scan area.

Figure 3:
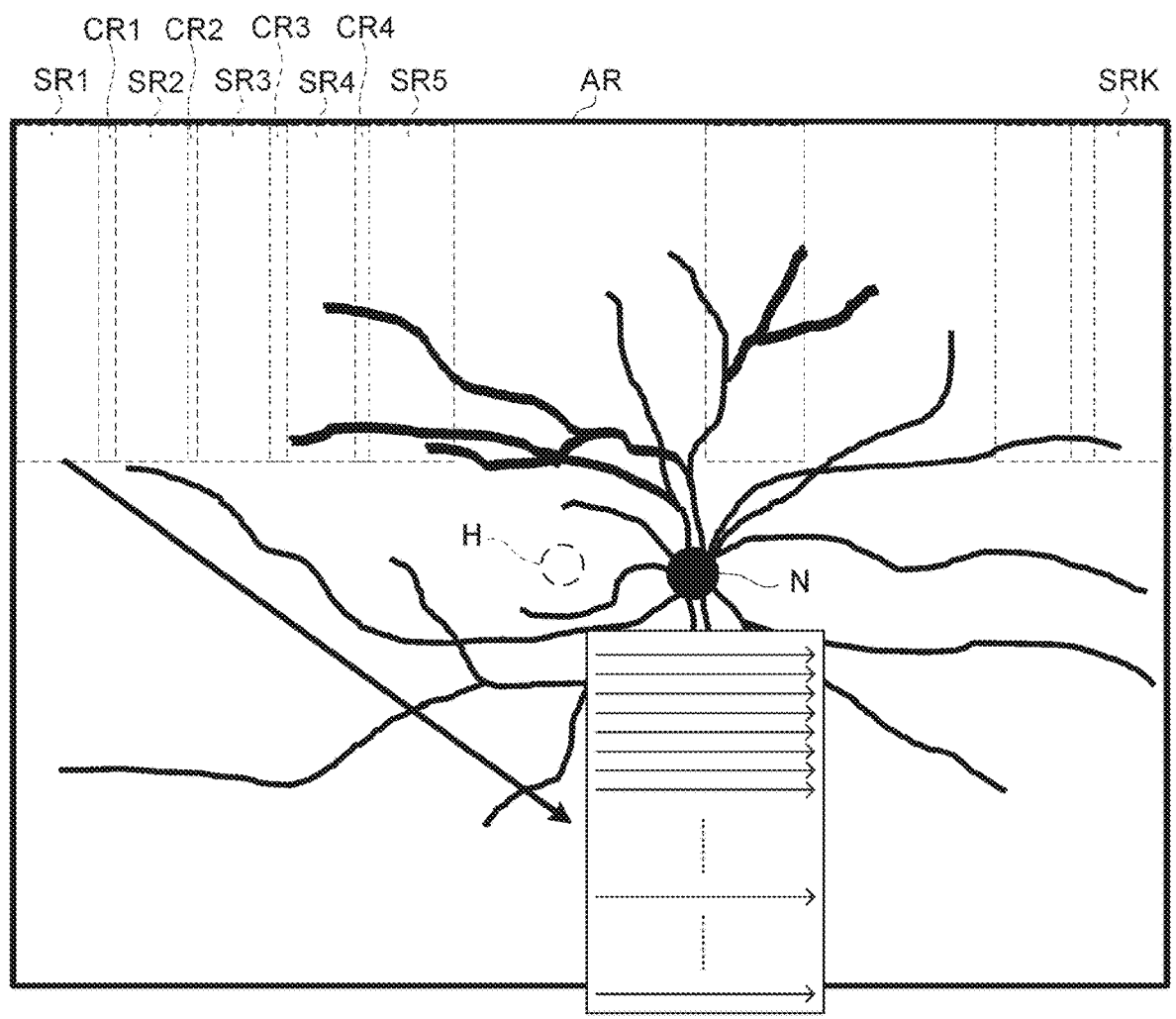
FIG. 3 is a schematic diagram for explaining processing performed by the ophthalmologic apparatus according to the embodiments.

FIG. 3 shows a diagram describing a scan mode according to the embodiments. FIG. 3 schematically represents a mode in which the entire scan area AR including the optic disc N and the macular region H is divided into a plurality of sub-scan areas and scanned.

The main controller 51 moves the sub-scan area (single scan area) to be scanned by controlling the movement mechanism 4 in accordance with the previously defined movement pattern. For example, the main controller 51 moves the sub-scan area to be scanned in the order of, for example, sub-scan areas SR1, SR2, SR3, . . . . At this time, adjacent sub-scan areas SRi and SR (i+1) have an overlapping area CRi (i=1, 2, 3, . . . ). When an image of the entire scan area AR is formed from a plurality of images obtained from a plurality of sub-scan areas, position matching of adjacent images can be performed using the overlapping area. The main controller 51 controls the optical system 2 so as to scan each sub-scan area based on the previously defined deflection pattern. In the example shown in FIG. 3, a raster scan is applied. Other examples of the deflection pattern include circle scan, concentric circle scan, radial scan, slit scan (one dimensional scan), and the like.

Further, the main controller 51 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

The rough focus adjustment is a kind of focus adjustment using the split indicator. The rough focus adjustment may be performed by determining the position of the focusing lens based on preliminary prepared information in which eye refractive powers and positions of the focusing lens provided in the observation optical system 20 and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement on the subject's eye E; searching the position of the focusing lens so as to maximize the interference intensity; and moving the focusing lens to the searched position.

To perform the optical path length difference adjustment, the optical system is controlled so that a predetermined position on the subject's eye E is a reference position of a measurement range in the depth direction. The control is performed on the above optical path length changing unit. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarized wave (polarization) state of the reference light is adjusted for optimizing the interference efficiency between the measurement light and the reference light.

Further, the main controller 51 includes a display controller 51A. The display controller 51A controls the display device (display unit) in the UI unit 8 or an external display apparatus (not shown) to display various types of information. Examples of the information displayed by the display controller 51A include information representing the state of the optical system 2, information representing the state of the movement mechanism 4, information representing a control content for the controller 5 or a control result of the controller 5, an image formed by the image forming unit 6, a processing result obtained by the data processor 7, and information for assisting the operation of the operation device in the UI unit 8.

(Storage Unit)

The storage unit 52 stores various types of data. Examples of the data stored in the storage unit 52 include image data of an OCT image, image data of a fundus image, scan data, image data of an anterior segment image, and subject's eye information. The subject's eye information includes information on the subject such as patient ID and name, and information on the subject's eye such as identification information of the left eye/right eye.

Further, the storage unit 52 stores an eyeball parameter 52A. The eyeball parameter 52A includes a parameter (standard value) defined by a known eyeball model such as a Gullstrand schematic eye. In some embodiments, the eyeball parameter 52A includes a parameter in which at least one of the parameters defined by a known eyeball model is replaced with the measured value of the subject's eye E. In this case, it means that the eyeball parameter 52A includes a parameter representing optical characteristics of the subject's eye E. Examples of the measured value include an axial length, a corneal thickness, a curvature radius of an anterior surface of cornea, a curvature radius of a posterior surface of cornea, an anterior chamber depth, a curvature radius of an anterior surface of a lens, a lens thickness, a curvature radius of a posterior surface of lens, a vitreous cavity length, a retinal thickness, and a choroid thickness. In some embodiments, the measured value is acquired by analyzing OCT data obtained by performing OCT measurement. The eyeball parameter 52A may include a parameter designated using the UI unit 8 described later.

In addition, the storage unit 52 stores various kinds of computer programs and data for operating the ophthalmologic apparatus 1.

<Image Forming Unit>

The image forming unit 6 forms an OCT image (tomographic image) of the subject's eye E from scan data acquired by scanning inside the eye with the measurement light using the optical scanner disposed at an optically substantially conjugate position with a predetermined site (for example, the pupil) of the subject's eye E. The image forming unit 6 performs signal processing such as the Fourier transform on sampling data obtained by sampling the detection signal from the detector in the interference optical system 40 with the DAQ. With this, the reflection intensity profile for A-line is formed. The above signal processing includes noise removal (noise reduction), filtering, fast Fourier transform (FFT), and the like. The reflection intensity profile for the A-line is an example of the A-scan data. The image forming unit 6 can form the reflection intensity profile for each A-line, and form B-scan data (two-dimensional scan data) by arranging a formed plurality of reflection intensity profiles in the B-scan direction (intersecting direction of the A-scan direction).

In some embodiments, the image forming unit 6 (or the data processor 7 described later) forms three-dimensional scan data by arranging the plurality of reflection intensity profiles formed for each A-line in the B-scan direction (for example, x direction) and a direction intersecting both of the A-scan direction and the B-scan direction (for example, y direction).

Further, the image forming unit 6 can form A-scan image (OCT image, image data) of the subject's eye E, by applying imaging processing to the reflection intensity profile in the A-line. The image forming unit 6 can form a B-scan image by arranging the plurality of A-scan images formed for each A-line in the B-scan direction (intersecting direction of the A-scan direction).

In some embodiments, the image forming unit 6 extracts data at a predetermined depth position (scan position) in each A-scan data, and forms C-scan data by arranging the extracted plurality of data in the B-scan direction (intersecting direction of the A-scan direction). In some embodiments, the image forming unit 6 extracts a pixel at a predetermined depth position (scan position) in each A-scan image, and forms a C-scan image by arranging the extracted plurality of pixels in the B-scan direction (intersecting direction of the A-scan direction).

In some embodiments, the function of the image forming unit 6 is realized by a processor. Note that "image data" and an "image" based on the image data may not be distinguished from each other in the present specification.

<Data Processor 7>

The data processor 7 executes various kind of data processing. Examples of the data processing include processing on the image data formed by the image forming unit 6 or another apparatus. Examples of this processing include image processing, image analyzing, image evaluation, diagnosis support, and the like. For example, the data processor 7 performs correction processing such as brightness correction of images and/or dispersion correction of images. Further, the data processor 7 performs various kinds of image processing and various kinds of analysis processing on fundus images or tomographic images. The data processor 7 can form volume data (voxel data) of the subject's eye E by performing known image processing such as interpolation processing for interpolating pixels between tomographic images. In the case of displaying an image based on the volume data, the data processor 7 performs rendering processing on the volume data so as to form a pseudo three-dimensional image viewed from a specific line-of-sight direction.

In addition, the data processor 7 can a C-mode image, a projection image, a shadowgram, or the like from the volume data. The C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set (for example, partial data corresponding to a specific layer) in a predetermined direction.

Further, the data processor 7 can form an image of the entire scan area AR by performing position matching of adjacent images on a plurality of images (tomographic images) obtained from a plurality of sub-scan areas. At this time, the data processor 7 can perform position matching of adjacent images using the overlapping area.

The data processor 7 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 7 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 7 forms an OCTA image by extracting information of a predetermined thickness at a desired site from a plurality of built emphasized images and building as an en-face image.

Further, the data processor 7 determines the focus state of the measurement light in fine focus adjustment control by analyzing the detection result of the interference light obtained by performing OCT measurement. For example, the main controller 51 performs repetitive OCT measurements while controlling the movement of the focusing lens in the interference optical system 40 according to a predetermined algorithm. The data processor 7 analyzes detection results of interference light repeatedly acquired by performing OCT measurements to calculate predetermined evaluation values relating to image quality of OCT images. The data processor 7 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light is appropriate. And the fine focus adjustment is continued until it is determined that the focus state of the measurement light is appropriate.

In some embodiments, the main controller 51 monitors the intensity of the interference signal (interference intensity, interference sensitivity) acquired sequentially while acquiring the interference signal by performing the repetitive OCT measurements described above. In addition, while performing this monitoring process, the focusing lens in the interference optical system 40 is moved to find the position of the focusing lens in which the interference intensity is maximized. With the fine focus adjustment thus performed, the focusing lens can be guided to the position where the interference intensity is optimized.

Further, the data processor 7 determines the polarization state of at least one of the measurement light and the reference light by analyzing the detection result of the interference light obtained by performing OCT measurement. For example, the main controller 51 performs repetitive OCT measurements while controlling the polarization controller according to a predetermined algorithm. In some embodiments, the main controller 51 controls the optical attenuator to change an attenuation of the reference light. The data processor 7 analyzes detection results of interference light repeatedly acquired by performing OCT measurements to calculate predetermined evaluation values relating to image quality of OCT images. The data processor 7 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light is appropriate. And the polarization adjustment is continued until it is determined that the polarization state of the measurement light is appropriate.

In some embodiments, the main controller 51 can monitor the interference intensity also in the polarization adjustment.

Further, the data processor 7 performs predetermined analysis processing on the detection result of the interference light acquired by performing OCT measurement or the OCT image formed based on the detection result. Examples of the predetermined analysis processing include specifying (identification) of a predetermined site (tissue, lesion) of the subject's eye E; calculation of a distance, area, angle, ratio, or density between designated sites (distance between layers, interlayer distance); calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

In some embodiments, the data processor 7 performs coordinate transformation on the pixel positions in the OCT image or the scan positions in the scan data so that the site in the eye in the acquired OCT image (tomographic image, scan data) is drawn in actual shape.

Here, a comparative example of the embodiments will be described.

Figure 4:
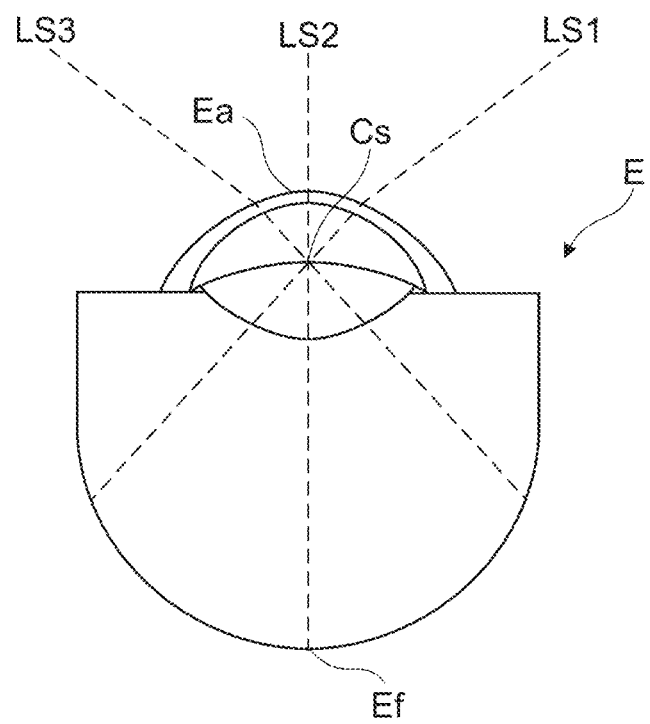
FIG. 4 is a schematic diagram for explaining processing performed by the ophthalmologic apparatus according to a comparative example of the embodiments.
Figure 5:
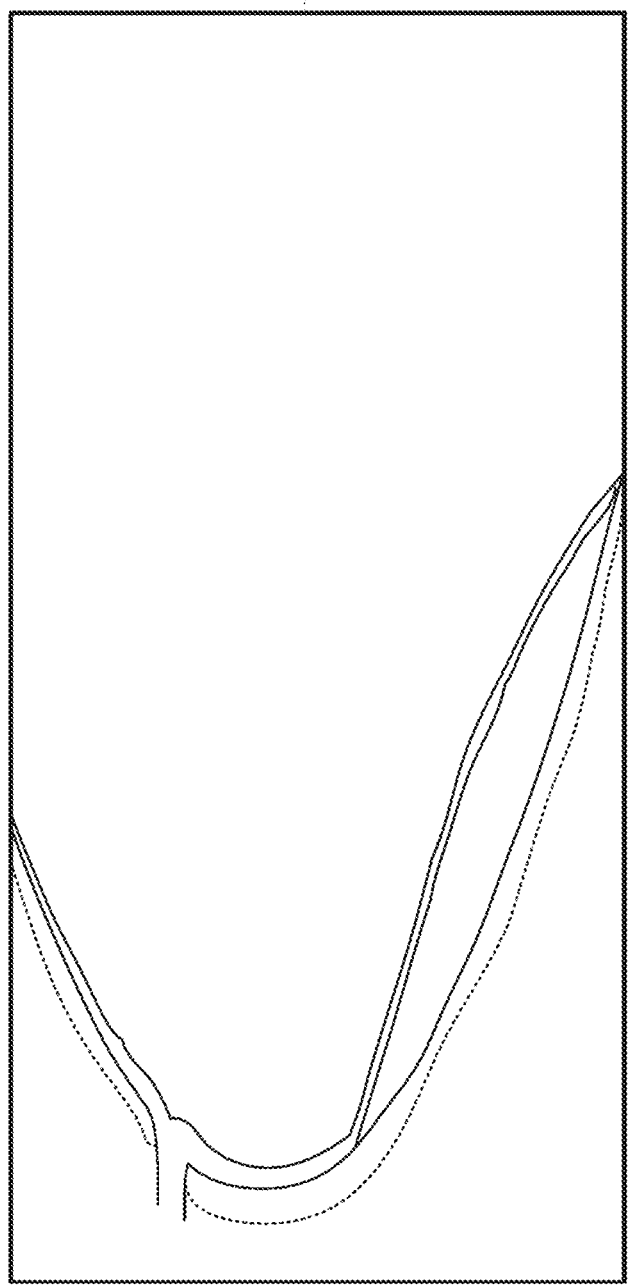
FIG. 5 is a schematic diagram for explaining processing performed by the ophthalmologic apparatus according to a comparative example of the embodiments.

FIGS. 4 and 5 show diagrams of comparative examples of the embodiments. FIG. 4 schematically shows the path of the measurement light incident on the subject's eye E. FIG. 5 shows an example of the tomographic image obtained by scanning with the measurement light incident on the subject's eye E through the path shown in FIG. 4.

The measurement light deflected by the optical scanner in the scan optical system 30, for example, is incident on the pupil of the subject's eye E, which is a scan center position, at various incident angles, as shown in FIG. 4. The measurement light incident on the subject's eye E is projected toward each part in the eye around the scan center position Cs set at the center of the pupil, for example.

An A-scan image is formed from the interference data obtained using the measurement light LS1 in FIG. 4, an A-scan image is formed from the interference data obtained using the measurement light LS2, and an A-scan image is formed from the interference data obtained using the measurement light LS3. The tomographic image IMG0 of the fundus shown in FIG. 5 is formed by arranging the plurality of A-scan images thus formed.

In this way, the A scan directions vary within the scan angle range centered on the scan center position Cs, and the shape of the site is deformed in the tomographic images in which the obtained plurality of A scan images are arranged in the horizontal direction. The wider the angle of view is, the greater the difference from the actual shape becomes.

Further, morphology information representing the morphology of the subject's eye E can be obtained from the positions of arbitrary pixels in the tomographic image. Examples of the morphology information include an intraocular distance (including a distance between layer regions), an area of region, a volume of region, a perimeter of region, a direction of site with reference to a reference position, an angle of site with reference to a reference direction, and a curvature radius of site.

For example, the intraocular distance as the morphology information can be obtained by measuring a distance between arbitrary two points in the tomographic image. In this case, the distance between the two points can be specified using the number of pixels in the tomographic image, and can be measured by multiplying the specified number of pixels by the pixel size specific to the apparatus. At this time, the same pixel size is adopted for all pixels in the tomographic image. However, as described above, the scan directions are different with the scan center position Cs as the center. Thereby, the pixel size in the horizontal direction of the tomographic image differs depending on the depth position in the scan direction. For example, in case that the depth range is 2.5 millimeters, when the same pixel size is adopted for all pixels in the tomographic image, there is a difference of about 13% in the scan length of the B-scan between the upper portion and the lower portion of the tomographic image, and when the depth range is 10 millimeters, there is a difference of about 50%.

Therefore, the data processor 7 according to the embodiments performs coordinate transformation on the pixel positions in the acquired OCT image or the scan positions in the scan data. Hereinafter, as the morphology information representing the morphology of the subject's eye E, the distance (thickness) of the layer region in the fundus Ef will be described as an example.

Figure 6:
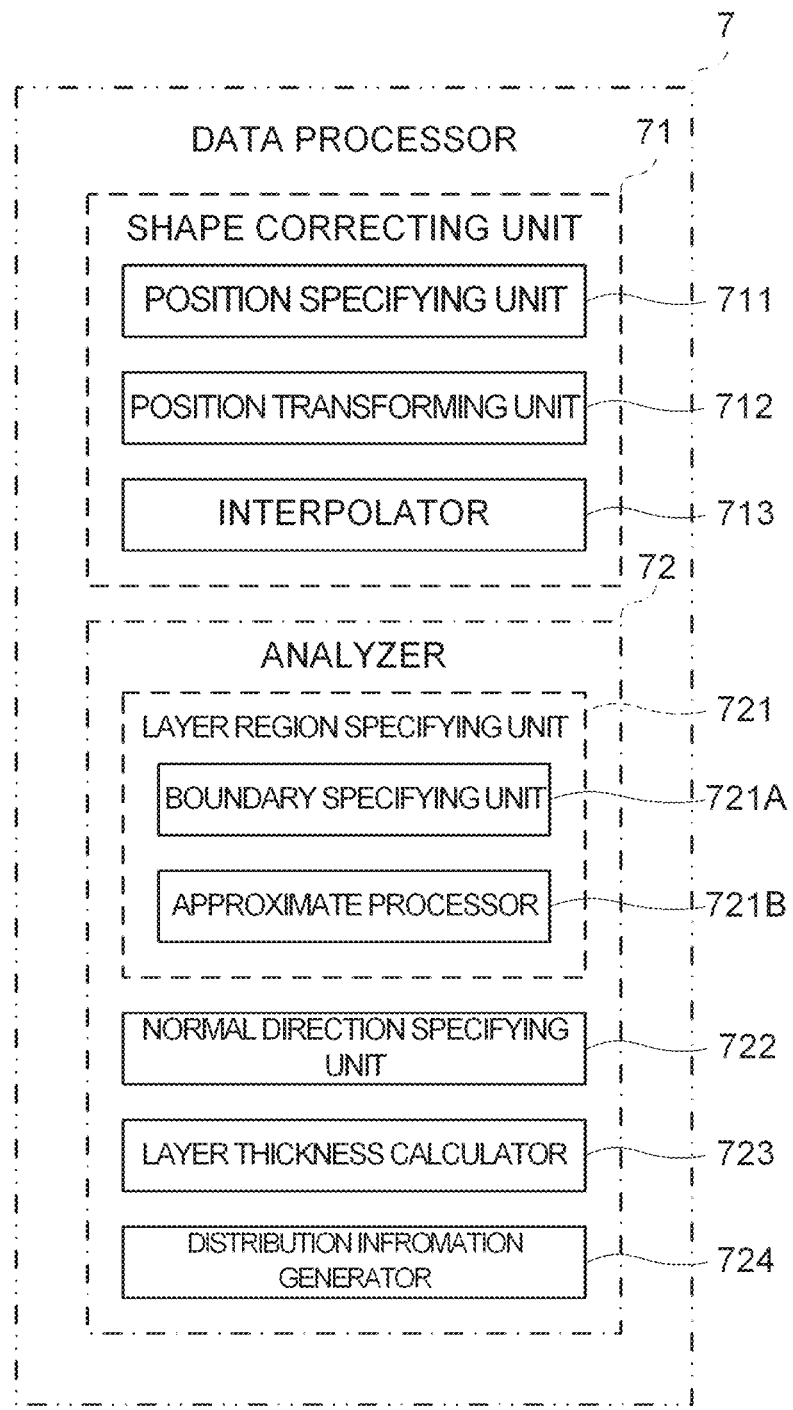
FIG. 6 is a schematic block diagram illustrating an example of the configuration of the ophthalmologic apparatus according to the embodiments.

FIG. 6 shows a block diagram of an example of the configuration of the data processor 7 according to the embodiments.

The data processor 7 includes a shape correcting unit 71 and an analyzer 72. The shape correcting unit 71 performs coordinate transformation on the pixel positions in the acquired OCT image or the scan positions in the scan data. The analyzer 72 performs predetermined analysis processing on the OCT data or the scan data, which is corrected by the shape correcting unit 71.

(Shape Correcting Unit)

The shape correcting unit 71 includes a position specifying unit 711, a position transforming unit 712, and an interpolator 713.

(Position Specifying Unit)

The position specifying unit 711 is configured to specify a transformation position along a traveling direction of the measurement light passing through the scan center position Cs (See FIG. 7), the transformation position corresponding to a pixel position in the acquired OCT image (or the scan position in the scan data). In some embodiments, the position specifying unit 711 uses the eyeball parameter 52A for performing processing for specifying the transformation position.

Figure 7:
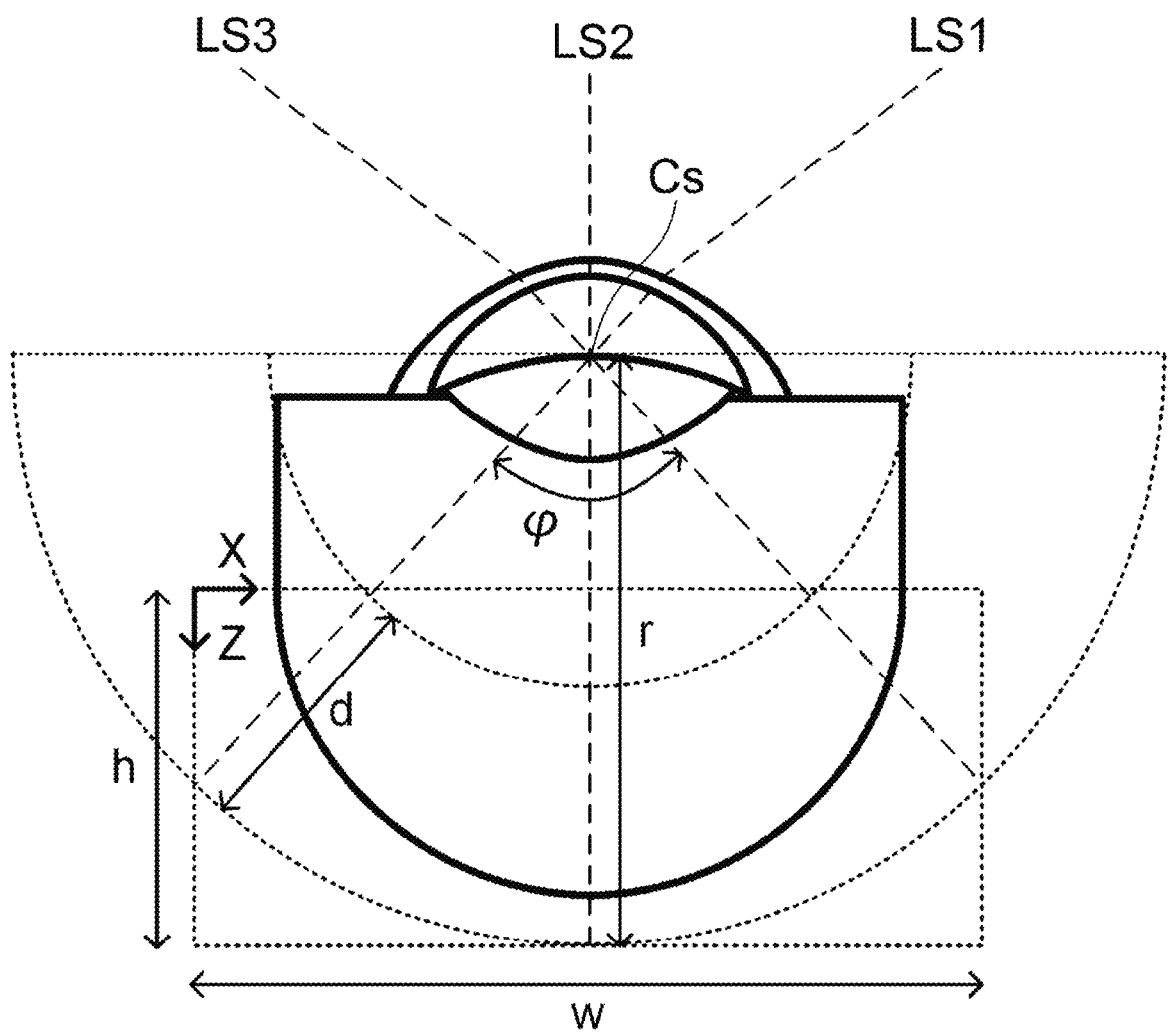
FIG. 7 is a schematic diagram for explaining processing performed by the ophthalmologic apparatus according to the embodiments.

FIG. 7 shows a diagram describing the operation of the position specifying unit 711 according to the embodiments. In FIG. 7, parts similarly configured to those in FIG. 4 are denoted by the same reference numerals, and the description thereof is omitted unless it is necessary.

Here, the scan angle is "φ", the scan radius is "r", the depth range in which OCT measurement can be performed is "d", the length of the tomographic image in the depth direction is "h", and the lateral length of the tomographic image is "w". The scan angle φ corresponds to the deflection angle of the measurement light around the scan center position Cs. The scan radius r corresponds to the distance from the scan center position Cs to a zero optical path length position where the measurement optical path length and the reference optical path length are substantially equal. The depth range d is a value (known) specific to the apparatus, the value being uniquely determined by the optical design of the apparatus.

The position specifying unit 711 specifies the transformation position (X, Z) in a second coordinate system from the pixel position (x, z) in a first coordinate system. The first coordinate system is a coordinate system having the origin at the upper left coordinate position in the OCT image (B-scan image). The first coordinate system is defined by an x coordinate axis having the B-scan direction as the x direction and a z coordinate axis, which is orthogonal to the x coordinate axis, having the A-scan direction as the z direction. The pixel position (x, z) in the OCT image is defined in the first coordinate system. The second coordinate system is defined by a Z coordinate axis (for example, second axis) and an X coordinate axis (for example, first axis). The Z coordinate axis has the traveling direction of the measurement light having the scan angle of 0 degree with respect to the measurement optical axis passing through a predetermined site (for example, fovea) in the fundus Ef, as the Z direction. The X coordinate axis has the B-scan direction orthogonal to the Z coordinate axis at the predetermined site, as the X direction. In the second coordinate system, a predetermined Z position is set as the origin of the Z coordinate axis so that the position of the scan radius r becomes the deepest portion in the measurement optical axis passing through the predetermined site (for example, the fovea). Further, a predetermined X position in the measurement optical axis passing through the predetermined site (for example, the fovea) set as the origin of the X coordinate axis so as to have a predetermined depth direction length d as described below. The transformation position (X, Z) is defined in the second coordinate system. The transformation position (X, Z) corresponds to the pixel position (x, z), and is a position along the traveling direction of the measurement light passing through the scan center position Cs (A-scan direction).

For the OCT image, the position specifying unit 711 specifies the transformation position (X, Z) based on the scan radius r of the A-scan direction, the scan angle φ, the depth range d in which the OCT measurement can be performed, and the pixel position (x, z). The position specifying unit 711 can specify at least one of the X component of the transformation position (component of the first axis direction) and the Z component of the transformation position (component of the second axis direction).

For the OCT image (tomographic image) which the number of A-scan lines is "N" (N is a natural number), the transformation position (X, Z), which corresponds to the pixel position (x, z) in the n-th (n is a natural number) A-scan line, is specified as shown in Equations (1) and (2).

[Equation 1]
$$X = \frac{w}{2} + (r - d + z) \times \sin\left(\frac{\varphi}{N} \times n - \frac{\varphi}{2}\right) \quad (1)$$

[Equation 2]
$$Z = (r - d + z) \times \cos\left(\frac{\varphi}{N} \times n - \frac{\varphi}{2}\right) - (r - d) \times \cos\frac{\varphi}{2} \quad (2)$$

Here, the length "h" in the depth direction of the OCT image, the length "w" in the horizontal direction of the OCT image, and the x component of the pixel position are expressed by Equations (3) to (5).

[Equation 3]
$$h = r - (r - d) \times \cos\frac{\varphi}{2} \quad (3)$$

[Equation 4]
$$w = 2r \times \sin\frac{\varphi}{2} \quad (4)$$

[Equation 5]
$$x = n \quad (5)$$

In Equations (1) and (2), the x coordinate of the pixel position is expressed by Equation (5). Thus, the position specifying unit 711 can specify the transformation position (X, Z) from the pixel position (x, z), based on the scan radius r, the scan angle φ, and the depth range d.

In some embodiments, for the scan data, the position specifying unit 711 can specify the transformation position (X, Z) based on the scan radius r in the A-scan direction, the scan angle φ, the depth range d in which the OCT measurement can be performed, and the scan position, in the same way as above.

In some embodiments, the scan radius r is specified by analyzing the detection result of the interference light obtained using the interference optical system 40. This allows to specify the transformation position (X, Z) that more accurately reflects the eyeball optical characteristics of subject's eye E.

In some embodiments, the position specifying unit 711 specifies the scan angle φ by performing ray trace processing on the measurement light based on the corneal shape information of the subject's eye E. Examples of the corneal shape information include a corneal curvature radius (curvature radius of an anterior surface of cornea, curvature radius of a posterior surface of cornea) and corneal thickness. This allows to specify the transformation position (X, Z) that more accurately reflects the eyeball optical characteristics of subject's eye E.

(Position Transforming Unit)

The position transforming unit 712 transforms the pixel position (x, z) in the OCT image into the transformation position (X, Z) specified by the position specifying unit 711. In some embodiments, for each of all pixel positions in the OCT image, the position specifying unit 711 specifies the transformation position and the position transforming unit 712 transforms the pixel position into the transformation position.

Figure 8:
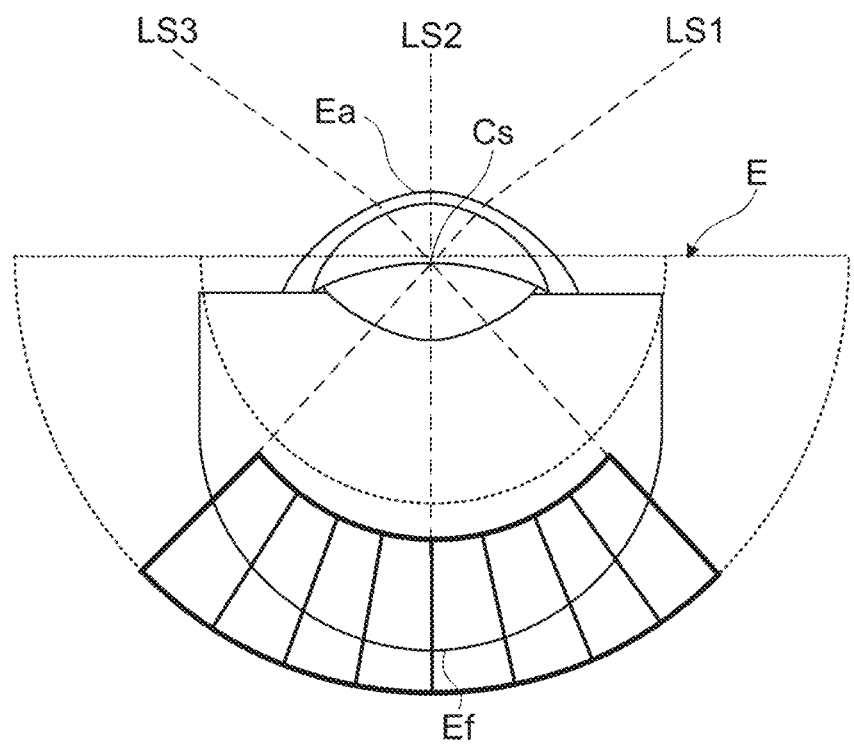
FIG. 8 is a schematic diagram for explaining processing performed by the ophthalmologic apparatus according to the embodiments.

This allows to arrange the A-scan images, which are acquired by performing A-scan, in the A-scan direction as shown in FIG. 8. Therefore, even if the angle of view is wide as in the tomographic image IMG1 shown in FIG. 9, the tomographic image in which the shape of the predetermined site is similar to the actual shape can be obtained.

Figure 9:
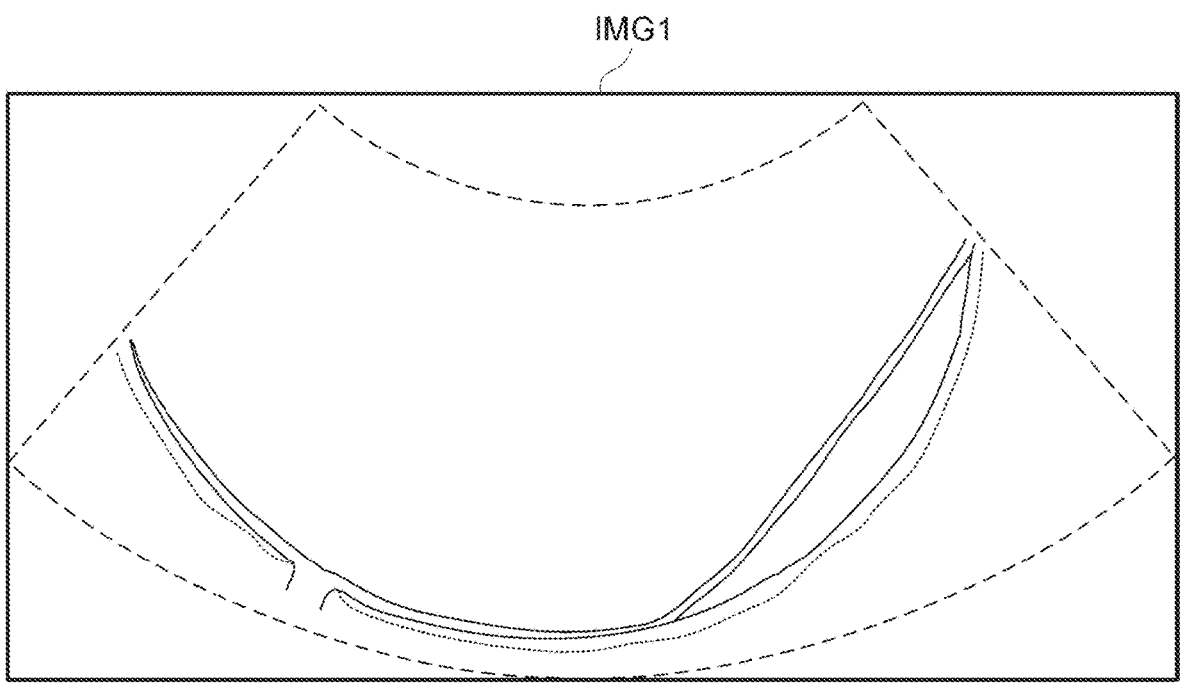
FIG. 9 is a schematic diagram for explaining processing performed by the ophthalmologic apparatus according to the embodiments.

For example, both of the tomographic image IMG0 shown in FIG. 5 and the tomographic image IMG1 shown in FIG. 9 are tomographic images of the fundus Ef with retinal detachments. In the tomographic image IMG1, a wide range of the detached state of the neural retina in the fundus Ef is depicted as an actual form. This allows to easily grasp the detached state as compared with the tomographic image IMG0.

(Interpolator)

The interpolator 713 interpolates pixels between the transformation positions. For example, intervals between the A-scan images adjacent to each other in which the pixel positions have been transformed into the transformation position varies depending on the distance from the scan center position Cs. The interpolator 713 interpolates pixel(s) between the A-scan images using a pixel in the A-scan images adjacent to each other according to the depth position in the A-scan image. As interpolation processing on pixels performed by the interpolator 713, a known method such as a nearest neighbor method, a bilinear interpolation method, or a bicubic interpolation method can be adopted. In some embodiments, the interpolator 713 interpolates pixels between the A-scan images adjacent to each other according to the distance from the scan center position Cs. For example, the interpolator 713 interpolates pixels between the A-scan images adjacent to each other by changing interpolation processing method according to the distance from the scan center position Cs.

In some embodiments, for the scan position in the scan data, the scan data is interpolated, in the same way as above.

(Analyzer)

The analyzer 72 shown in FIG. 6 includes a layer region specifying unit 721, a normal direction specifying unit 722, a layer thickness calculator 723, and a distribution information generator 724. The layer region specifying unit 721 includes a boundary specifying unit 721A and an approximate processor 721B.

(Layer Region Specifying Unit)

The layer region specifying unit 721 analyzes the OCT image in which the pixel positions have been transformed by the shape correcting unit 71 (position transforming unit 712) (OCT image in which pixels are interpolated by the interpolator 713) to specify a predetermined layer region in the fundus Ef (retina). Examples of the layer region include a layer in the retina, a Bruch's membrane, a choroid, a sclera. Examples of the layer in the retina include a retinal pigment epithelium layer, a photoreceptor layer, an external limiting membrane, an outer nuclear layer, an outer plexiform layer, an inner nuclear layer, an inner plexiform layer, a ganglion cell layer, a nerve fiber layer, and an inner limiting membrane.

The layer region specifying unit 721 specifies a plurality of pixels included in an image region corresponding to the predetermined layer region, based on pixel values of the OCT image of the fundus Ef corrected by the shape correcting unit 71. In some embodiments, the layer region specifying unit 721 specifies a region of pixels, in which a change in pixel value of adjacent pixels in the OCT image is equal to or less than a predetermined first threshold value, as a layer region to be specified.

(Boundary Specifying Unit)

The boundary specifying unit 721A analyzes the OCT image as described above to specify a boundary (boundary region) of the layer region described above. Examples of the boundary of the layer region include any of the above boundaries of layers in the retina, the boundary of the Bruch's membrane, the boundary of the choroidal, the boundary of the sclera, the boundary of the vitreous.

In some embodiments, the boundary specifying unit 721A specifies a region of pixels, in which a change in pixel value of adjacent pixels in the OCT image is equal to or greater than a predetermined second threshold value, as a boundary of the layer region. In some embodiments, the boundary specifying unit 721A specifies the image region between the two layer regions specified by the layer region specifying unit 721 as the boundary of the layer region.

When the OCT image is a two-dimensional image, the boundary specifying unit 721A specifies a boundary line of the layer region specified by the layer region specifying unit 721. In this case, the boundary line specified by the boundary specifying unit 721A may be a one-dimensional or two-dimensional image region.

When the OCT image is a three-dimensional image, the boundary specifying unit 721A specifies a boundary surface of the layer region specified by the layer region specifying unit 721. In this case, the boundary surface specified by the boundary specifying unit 721A may be a one-dimensional, two-dimensional, or three-dimensional image region.

(Approximate Processor)

The approximate processor 721B performs approximate processing on the layer region specified by the layer region specifying unit 721 (or the boundary specified by the boundary specifying unit 721A).

For example, in case that the OCT image is a two-dimensional image, the approximate processor 721B obtains an approximate curve of the boundary (boundary line) specified by the boundary specifying unit 721A. The approximate processor 721B obtains an approximate curve based on the pixels of the specified boundary region or the peripheral region thereof. This approximate curve can be obtained by an arbitrary method. For example, the approximate processor 721B approximates the above boundary using a known curve such as a spline curve, a linear approximation curve, a logarithmic approximation curve, a polynomial approximation curve, a power approximation curve, an exponential approximation curve, or a moving average approximation curve.

For example, in case that the OCT image is a three-dimensional image, the approximate processor 721B obtains an approximate surface (or approximate curve) of the boundary (boundary surface) specified by the boundary specifying unit 721A. The approximate processor 721B obtains an approximate curved surface based on the pixels of the specified boundary region or the peripheral region thereof. This approximate curved surface can be obtained by an arbitrary method. For example, the approximate processor 721B approximates the above boundary using a known curved surface such as a spline curved surface, a linear approximation curved surface, a logarithmic approximation curved surface, a polynomial approximation curved surface, a power approximation curved surface, an exponential approximation curved surface, a moving average approximation curved surface.

(Normal Direction Specifying Unit)

The normal direction specifying unit 722 specifies a normal direction for each of the two or more incident positions of the measurement light on the fundus Ef. Specifically, the normal direction specifying unit 722 specifies the normal direction for each of two or more positions on the layer region specified by the layer region specifying unit 721. In the embodiments, it is assumed that the approximate curve or the approximate curved surface of the layer region (or its boundary) obtained by the approximate processor 721B is information representing the shape of the fundus Ef, and the normal direction specifying unit 722 specifies the normal direction for each of the two or more positions on the approximate curve or the approximate curved surface of the boundary of the layer region. This allows to obtain the normal direction corresponding to the shape of the fundus Ef.

The normal direction specifying unit 722 can specify the normal direction using a known processing performed on an arbitrary position on the curve or the curved surface.

(Layer Thickness Calculator)

The layer thickness calculator 723 calculates, as a layer thickness, a distance in the normal direction specified by the normal direction specifying unit 722 for a predetermined layer region in the fundus Ef. In some embodiments, the layer thickness calculator 723 calculates the distance in the normal direction in the layer region specified by the layer region specifying unit 721. In some embodiments, the distance in the normal direction in the layer region of the upper layer or the lower layer in the z direction with respect to the incident position where the normal direction is specified is calculated.

The layer thickness calculator 723 can calculate the distance in the normal direction for the two or more positions in the layer region to be calculated. Further, the layer thickness calculator 723 can calculate the distance in the normal direction at a predetermined position for a predetermined layer region.

For example, the distance between the two points can be specified using the number of pixels in the tomographic image, and can be measured by multiplying the specified number of pixels by the pixel size specific to the apparatus. At this time, the same pixel size is adopted for all pixels in the tomographic image. The layer thickness calculator 723 calculates the above distance by counting the number of pixels between the two points on the normal in the specified normal direction.

(Distribution Information Generator)

The distribution information generator 724 generates distribution information representing a distribution of the distance (thickness) of the layer region calculated by the layer thickness calculator 723. The distribution information is information representing the distance of the layer region for each A-scan position. The distribution information may be information representing the distance of the layer region for each representative position of the two or more A-scan positions. The distribution information generator 724 can generate the distribution information by associating the distances of the layer region calculated by the layer thickness calculator 723 with the A-scan positions (incident positions of the measurement light). The distribution information generator 724 can generate two-dimensional or three-dimensional distribution information.

The display controller 51A displays an image corresponding to the distribution information generated by the distribution information generator 724 on the display device in the UI unit 8. In some embodiments, the display controller 51A displays an image corresponding to the distribution information in a display mode according to the distance (thickness) of the layer region calculated by the layer thickness calculator 723 on the display device in the UI unit 8. Examples of the image corresponding to the distribution information include an image in which a pixel with color (or brightness) corresponding to the distance of the layer region associated with the A-scan position for each A-scan position are arranged.

In some embodiments, the display controller 51A displays an image corresponding to the distribution information on the display device so that the display mode differs between the pixels at the A-scan positions with distances of the layer region greater than or equal to a predetermined reference value and the pixels at the A-scan positions with distances of the layer region below the reference value. Examples of the predetermined reference value include a statistic (mean value, median value, mode value, minimum value, maximum value, etc.) of the distances of the layer region.

In some embodiments, the display controller 51A displays an image corresponding to the distribution information on the display device so that the display mode differs between the pixels at the A-scan positions at distances of the layer region within a predetermined range including a predetermined reference value and the pixels at the A-scan positions at distances of the layer region outside the range.

Further, the display controller 51A can display an image representing the distribution information on the display device so as to be superimposed on the image of the subject's eye E or another measurement result of the subject's eye E. Examples of the image of the subject's eye E include an image (OCT image) of the subject's eye E formed by the image forming unit 6, and a corrected image of the subject's eye E whose pixel positions have been transformed by the data processor 7. Examples of the another measurement result of the subject's eye E include a result of a kinetic perimetry of the subject's eye E and a result of a static perimetry of the subject's eye E.

It should be noted that the analyzer 72 can obtain not only the distance of the layer region but also the distance between any two points in the eye. That is, the analyzer 72 obtains an intraocular distance between predetermined sites in the subject's eye E based on the OCT image transformed by the position transforming unit 712. For example, the analyzer 72 specifies the predetermined sites in the eye by analyzing the transformed OCT image, and obtains the intraocular distance described above based on the distance between the specified sites.

Examples of the intraocular distance between the predetermined sites include a distance between designated sites (tissues, layer regions), an axial length, and a distance from a scan center position of the measurement light, which is set at the center of the pupil, or the like, to a retina. In case that the axial length is obtained as the intraocular distance, the analyzer 72 obtains the axial length based on a distance from a site corresponding to a corneal apex to a site corresponding to the retina.

The data processor 7 that functions as above includes, for example, a processor described above, a RAM, a ROM, a hard disk drive, a circuit board, and the like. In a storage device such as the hard disk drive, a computer program for causing the processor to execute the functions described above is stored in advance.

<User Interface Unit>

The user interface (UI) unit 8 has a function for exchanging information between a user and the ophthalmologic apparatus 1. The user interface unit 8 includes a display device and an operation device (an input device). The display device includes, for example, a liquid crystal display (LCD). The operation device includes various hardware keys and/or various software keys. Upon receiving the operation content for the operation device, the controller 5 can output a control signal corresponding to the operation content to each part of the ophthalmologic apparatus 1. At least a part of the display device and at least a part of the operation device may be configured integrally. One example of this is the touch panel display.

As described above, the display controller 51A controls the display device in the UI unit 8 to display various images. In particular, the display controller 51A can display the tomographic image formed by the image forming unit 6 or the tomographic image after processing executed by the data processor 7 on the display device. The display controller 51A can simultaneously display the tomographic image formed by the image forming unit 6 and the tomographic image after processing executed by the data processor 7 on the same screen of the display device. Examples of the tomographic image after processing executed by the data processor include a tomographic image transformed by the position transforming unit 712, a tomographic image interpolated by the interpolator 713, and an image after processing executed by the analyzer 72.

The shape correcting unit 71 is an example of the "correcting unit" according to the embodiments. The layer region specifying unit 721 is an example of the "region specifying unit" according to the embodiments. The normal direction specifying unit 722 is an example of the "direction specifying unit" according to the embodiments. The layer thickness calculator 723 is an example of the "calculator" according to the embodiments. The display device in the UI unit 8 is an example of the "display device" according to the embodiments. The interference optical system 40, the scan optical system 30, and the image forming unit 6 (or the data processor 7) are an example of the "OCT unit" according to the embodiments.

[Operation]

The operation of the ophthalmologic apparatus 1 according to the embodiments will be described.

Figure 10:
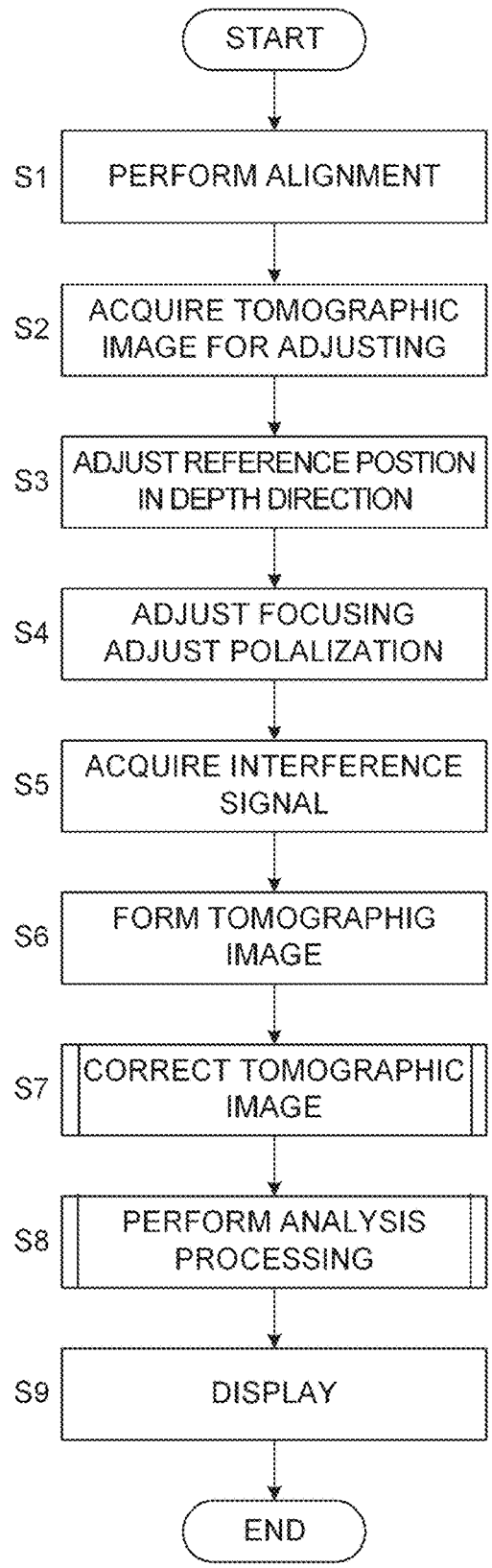
FIG. 10 is a schematic diagram illustrating an example of an operation of the ophthalmologic apparatus according to the embodiments.
Figure 11:
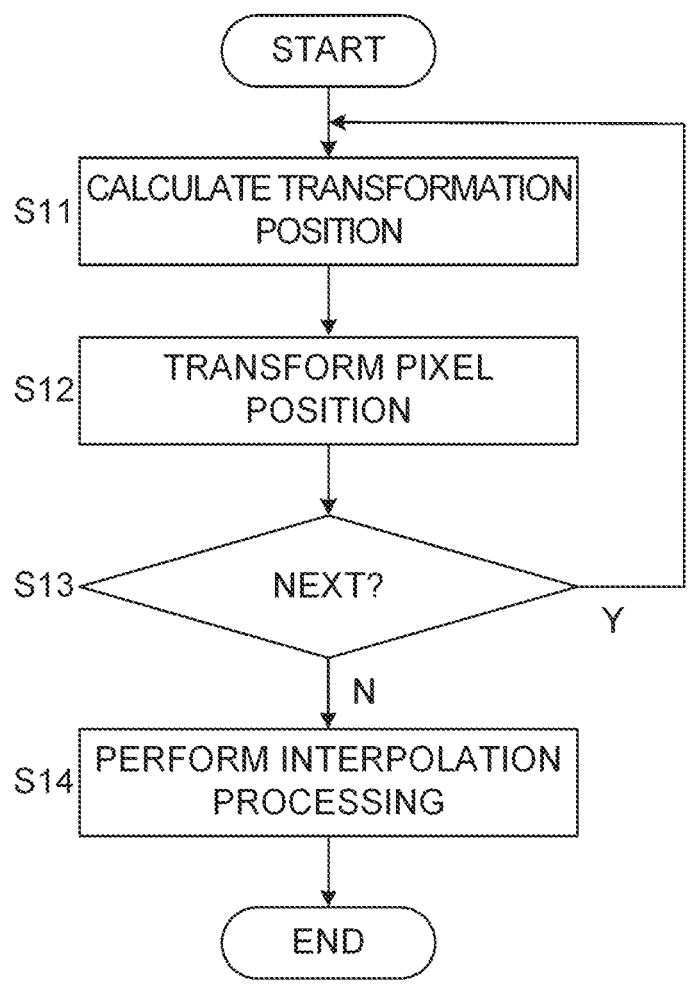
FIG. 11 is a schematic diagram illustrating an example of an operation of the ophthalmologic apparatus according to the embodiments.
Figure 12:
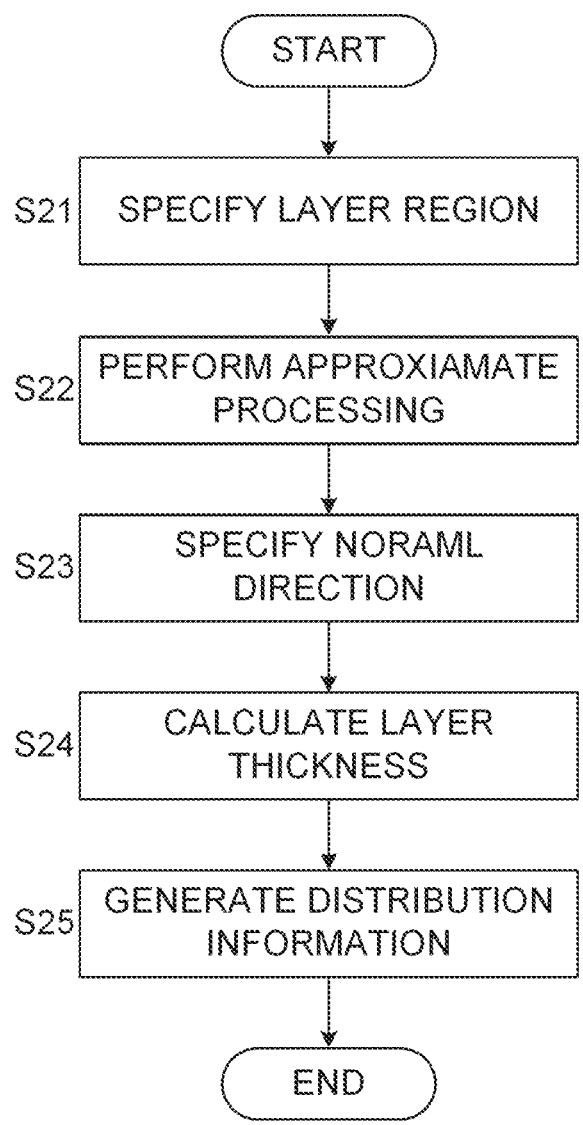
FIG. 12 is a schematic diagram illustrating an example of an operation of the ophthalmologic apparatus according to the embodiments.

FIGS. 10 to 12 show examples of the operation of the ophthalmologic apparatus 1 according to the embodiments. FIGS. 10 to 12 show flowcharts of the examples of the operation of the ophthalmologic apparatus 1 according to the embodiments. FIG. 11 shows a flowchart of an example of the operation of step S7 in FIG. 10. FIG. 12 shows a flowchart of an example of the operation of step S8 in FIG. 10. The storage unit 52 stores computer programs for realizing the processing shown in FIGS. 10 to 12. The main controller 51 operates according to the computer programs, and thereby the main controller 51 performs the processing shown in FIGS. 10 to 12.

(S1: Perform Alignment)

The main controller 51 performs alignment.

For example, the main controller 51 controls the alignment system (not shown) to project the alignment indicator onto the subject's eye E. At this time, a fixation light flux is projected onto the subject's eye E at a predetermined projected position (for example, a projected position on the measurement optical axis O) by the fixation optical system 50. The main controller 51 controls the xyz movement mechanism 4A based on the movement amount of the optical system 2 to relatively move the optical system 2 with respect to the subject's eye E by the movement amount. The movement amount is specified based on the receiving light image obtained using the observation optical system 20. The main controller 51 repeatedly performs this processing.

In some embodiments, the alignment rough adjustment and the alignment fine adjustment are performed after the alignment in step S1 is completed.

(S2: Acquire Tomographic Image for Adjustment)

The main controller 51 controls to project the fixation light flux for OCT measurement at a position on the measurement optical axis O on the fundus Ef, for example.

Subsequently, the main controller 51 controls the scan optical system 30 and interference optical system 40 to perform OCT provisional measurement, and to acquire a tomographic image for adjustment for adjusting the reference position of the measurement range in the depth direction. Specifically, the main controller 51 controls the optical scanner in the scan optical system 30 to deflect the measurement light generated based on the light emitted from the OCT light source and to scan a predetermined site (for example, fundus Ef) of the subject's eye E with the deflected measurement light. The detection result of the interference light obtained by scanning with the measurement light is sent to the image forming unit 6 after being sampled in synchronization with the clock. The image forming unit 6 forms the tomographic image (OCT image) of the subject's eye E from the obtained interference signal.

In some embodiments, the main controller 51 controls the driver 4D to rotate the optical system 2 within a predetermined movement angle range using the swing mechanism 4B and to perform the OCT measurement.

(S3: Adjust Reference Position in Depth Direction)

Subsequently, the main controller 51 adjusts the reference position of the measurement range in the depth direction (z direction).

For example, the main controller 51 controls the data processor 7 to specify a predetermined site (for example, sclera) in the tomographic image obtained in step S2, and sets a position separated by a predetermined distance in the depth direction from the specified position of the predetermined site as the reference position of the measurement range. The main controller 51 controls the optical path length changing unit (not shown) according to the reference position. Alternatively, a predetermined position determined in advance so that the optical path lengths of the measurement light and the reference light substantially coincide may be set as the reference position of the measurement range.

(S4: Adjust Focusing, Adjust Polarization)

Next, the main controller 51 performs control of adjusting focusing and of adjusting polarization.

For example, the main controller 51 controls the scan optical system 30 and the interference optical system 40 to perform the OCT measurement after moving the focusing lens by a predetermined distance. Here, the focusing lens is arranged between the scan optical system 30 and the beam splitter M2. The main controller 51 controls the data processor 7 to determine the focus state of the measurement light based on the detection result of the interference light acquired by performing OCT measurement, as described above. When it is determined that the focus state is not appropriate based on the determination result obtained by the data processor 7, the main controller 51 controls the movement of the focusing lens again and repeats this until it is determined that the focus state of the measurement light is appropriate.

Further, for example, the main controller 51 controls the polarization controller (not shown) to change the polarization state of at least one of the light from OCT light source and the measurement light by a predetermined amount. And then, the main controller 51 controls the scan optical system 30 and the interference optical system 40 to perform OCT measurement and controls the image forming unit 6 to form the OCT image on the basis of the acquired detection result of the interference light. The main controller 51 controls the data processor 7 to determine the image quality of the OCT image acquired by performing the OCT measurement, as described above. When it is determined that the polarization state is not appropriate based on the determination result obtained by the data processor 7, the main controller 51 controls the polarization controller again and repeats this until it is determined that the polarization state is appropriate.

(S5: Acquire Interference Signal)

Subsequently, the main controller 51 controls the driver 4D to start rotating the optical system 2 within the predetermined movement angle range using the swing mechanism 4B. Further, the main controller 51 controls the scan optical system 30 and interference optical system 40 to perform OCT measurement, while the optical system 2 is rotating. The detection result of the interference light acquired by performing OCT measurement is sampled by the DAQ and is stored as the interference signal in the storage unit 52 or the like.

(S6: Form Tomographic Image)

Next, the main controller 51 controls the image forming unit 6 to form the data set group of the A-scan image data of the subject's eye E based on the interference signal acquired in step S5. The image forming unit 6 forms the tomographic image as shown in FIG. 5, by arranging the formed A-scan images in the B-scan direction.

(S7: Correct Tomographic Image)

The main controller 51 corrects the tomographic image, which is formed in step S6, as described above using the eyeball parameter 52A stored in the storage unit 52. Details of step S7 will be described later. This allows to acquire the tomographic image in which the A-scan images are arranged in the A-scan direction.

(S8: Perform Analysis Processing)

Subsequently, the main controller 51 controls the analyzer 72 to analyze the tomographic image corrected in step S7. Details of step S8 will be described later.

(S9: Display)

Figure 13:
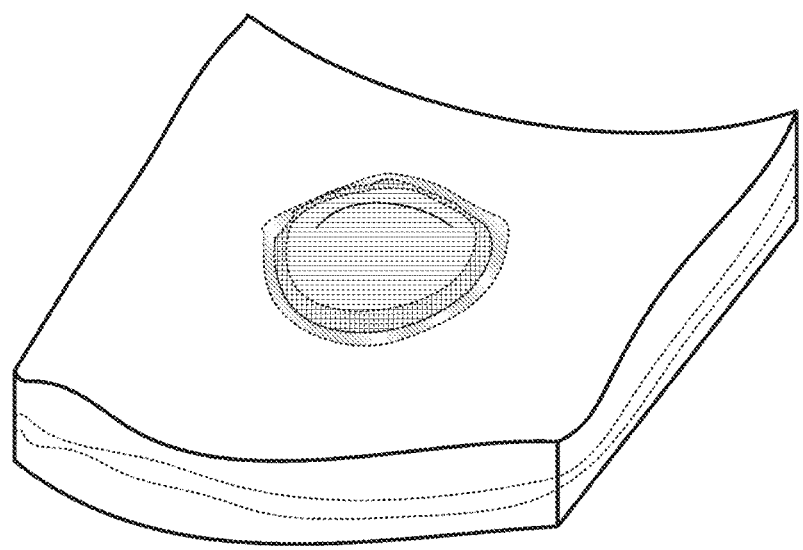
FIG. 13 is a schematic diagram illustrating an example of an operation of the ophthalmologic apparatus according to the embodiments.
Figure 14:
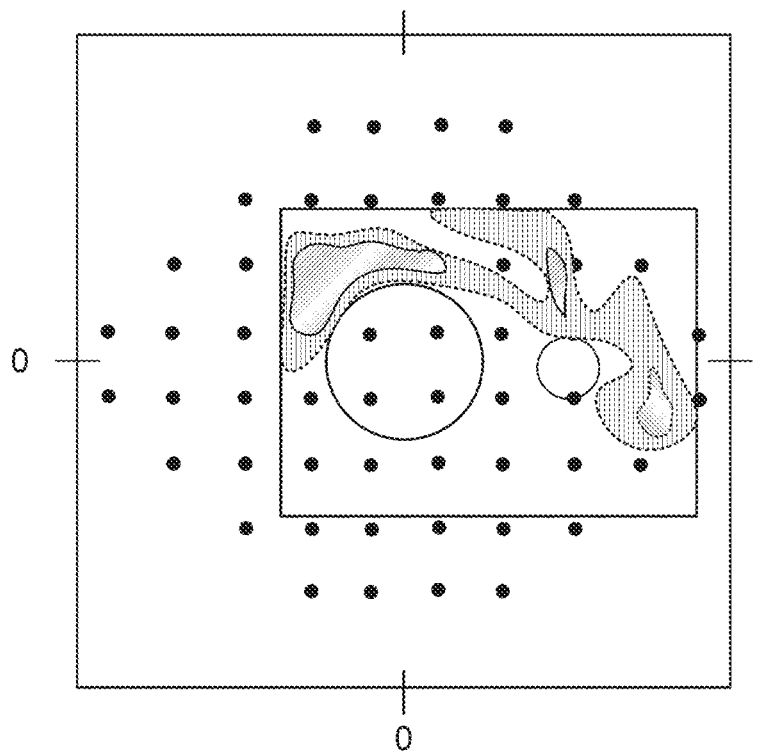
FIG. 14 is a schematic diagram illustrating an example of an operation of the ophthalmologic apparatus according to the embodiments.

The main controller 51 (display controller 51A) displays the result obtained by performing analysis processing in step S8 on the display device (see FIG. 13 or FIG. 14).

In some embodiments, the main controller 51 associates the A-scan positions with the pixels in the three-dimensional tomographic image of the fundus Ef of the subject's eye, and superimposes the pixels whose display mode has been changed according to the thickness of the layer region for each A-scan position and displays them on the display device, as shown in FIG. 13. This allows to accurately grasp a correct thickness of the layer region, for the peripheral part of the fundus or when the shape of the fundus is deformed. In particular, this allows to accurately grasp the thinned layer region or the edema in the fundus Ef.

In some embodiments, the main controller 51 associates the A-scan positions with the measurement points of the result of the static perimetry centered on the fixation point, and superimposes the pixels whose display mode has been changed according to the thickness of the layer region for each A-scan position and displays them on the display device, as shown in FIG. 14. This allows to accurately grasp a correct thickness of the layer region in connection with the result of the perimetry, for the peripheral part of the fundus or when the shape of the fundus is deformed.

This terminates the operation of the ophthalmologic apparatus 1 (END).

In step S7 in FIG. 10, the following processing is performed as shown in FIG. 11.

(S11: Calculate Transformation Position)

In step S7, the main controller 51 controls the position specifying unit 711 to specify the transformation position corresponding to the pixel position in the tomographic image formed in step S6. The position specifying unit 711 specifies the transformation position corresponding to the pixel position in the tomographic image, as described above.

(S12: Transform Pixel Position)

Subsequently, the main controller 51 controls the position transforming unit 712 to transform the pixel position in the tomographic image into the transformation position calculated in step S11.

(S13: Next?)

The main controller 51 determine whether or not the next pixel position should be transformed.

When it is determined that the next pixel position should be transformed (S13: Y), the operation of the ophthalmologic apparatus proceeds to step S11. When it is determined that the next pixel position should not be transformed (S13: N), the operation of the ophthalmologic apparatus proceeds to step S14.

Through steps S11 to S13, for each pixel position of the tomographic image, specifying the transformation position and transforming to the specified transformation position are performed.

(S14: Perform Interpolation Processing)

When it is determined that the next pixel position should not be transformed in step S13 (S13: N), the main controller 51 controls the interpolator 713 to interpolate the pixels between the A-scan images adjacent to each other, A-scan images having been transformed into the transformation positions in step S12.

This terminates the processing of step S7 in FIG. 10 (END).

In step S8 in FIG. 10, the following processing is performed as shown in FIG. 12.

(S21: Specify Layer Region)

In step S8, the main controller 51 controls the layer region specifying unit 721 to specify the layer region in the tomographic image corrected in step S7. The layer region specifying unit 721 specifies the predetermined layer region in the fundus Ef, as described above.

(S22: Perform Approximate Processing)

Next, the main controller 51 controls the approximate processor 721B to perform approximate processing on the layer region (boundary) specified in step S21. The approximate processor 721B performs approximate processing on the layer region specified by the layer region specifying unit 721 (or the boundary specified by the boundary specifying unit 721A), as described above.

(S23: Specify Normal Direction)

Next, the main controller 51 controls the normal direction specifying unit 722 to specify the normal directions at the two or more positions based on the approximate curve (approximate curved surface) of the layer region (boundary) acquired by performing approximate processing in step S22. The normal direction specifying unit 722 specifies the normal direction for each of the two or more positions on the approximate curve or the approximate curved surface of the layer region (or its boundary), as described above.

(S24: Calculate Layer Thickness)

Subsequently, the main controller 51 controls the layer thickness calculator 723 to calculate the distance in the normal direction specified in step S23 for the layer region specified in step S21. The layer thickness calculator 723 calculates the distance in the normal direction of the layer region, as described above.

(S25: Generate Distribution Information)

Further, the main controller 51 generates the distribution information by associating the distance (thickness) of the layer region calculated in step S24 with the A-scan position. The generated distribution information is displayed on the display device, as shown in FIG. 13 or FIG. 14.

This terminates the processing of step S8 in FIG. 10 (END).

MODIFICATION EXAMPLE

In the embodiments described above, the case has been described in which the two-dimensional OCT image (or the two-dimensional scan data) is corrected by performing coordinate transformation. However, the configuration according to the embodiments is not limited thereto. The ophthalmologic apparatus according to the embodiments can correct three-dimensional OCT data (or the three-dimensional scan data), as in the embodiments described above. Hereinafter, an ophthalmologic apparatus according to a modification example of the embodiments will be described focusing on differences from the embodiments.

The configuration of the ophthalmologic apparatus according to the modification example of the embodiments is similar to the configuration of the ophthalmologic apparatus 1 according to the embodiments. Therefore, the description thereof will be omitted.

The data processor according to the present modification example performs processing for specifying the transformation position in the three-dimensional space, or the like.

The position specifying unit 711 according to the present modification example specifies the transformation position along the traveling direction of the measurement light passing through the scan center position Cs, the transformation position corresponding to the pixel position in the acquired OCT image (or the scan position in the scan data). In some embodiments, the position specifying unit 711 specifies the transformation position using the eyeball parameter 52A.

Figure 15:
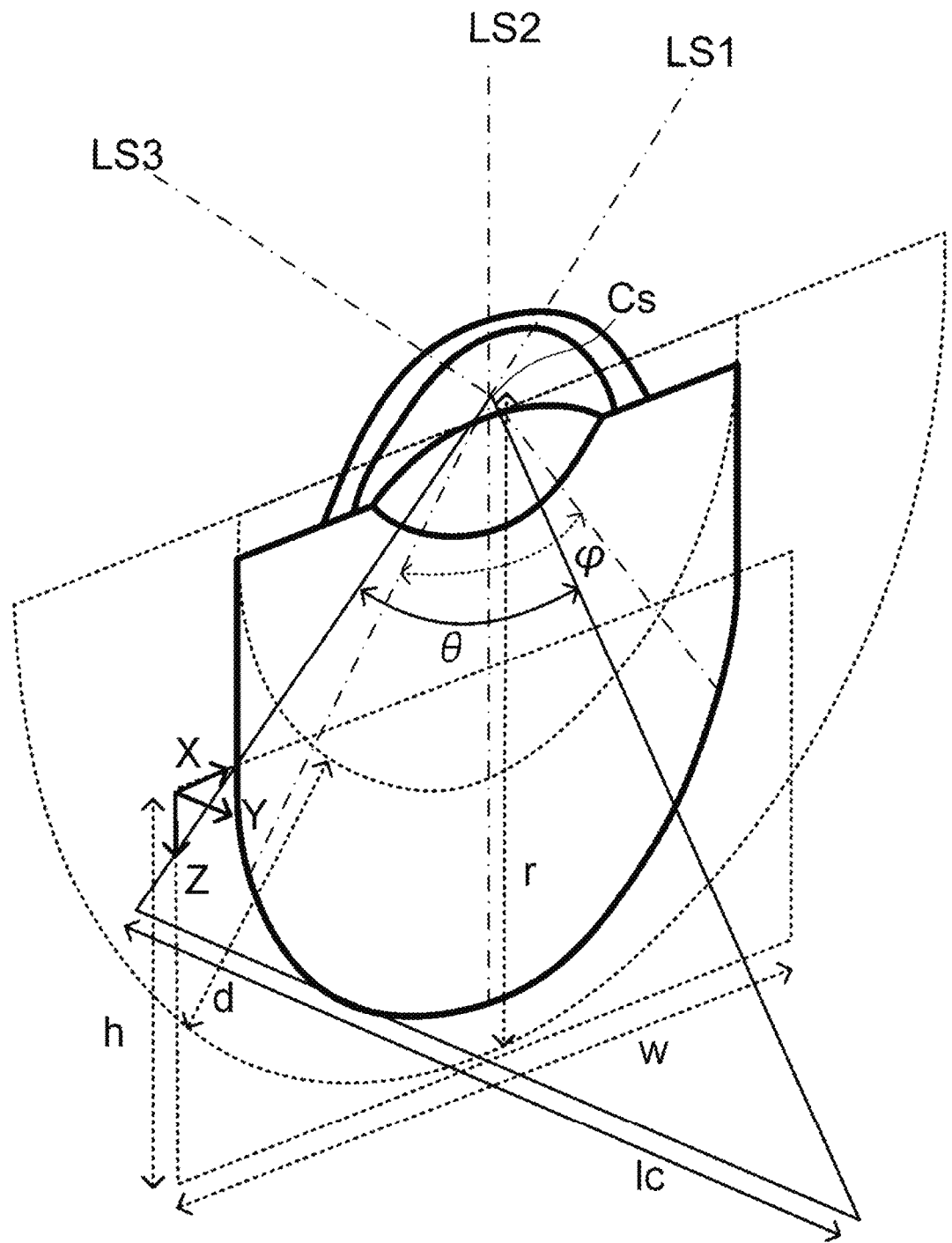
FIG. 15 is a schematic diagram for explaining processing performed by the ophthalmologic apparatus according to a modification example of the embodiments.

FIG. 15 shows a diagram describing the operation of the position specifying unit 711 according to the present modification example. In FIG. 15, parts similarly configured to those in FIG. 7 are denoted by the same reference numerals, and the description thereof is omitted unless it is necessary.

In FIG. 15, a Y plane is defined in addition to the X plane and the Z plane in FIG. 7. In addition to the parameters shown in FIG. 7, the central angle in the C-scan direction is "θ", and the length in the C-scan direction is "lc".

The position specifying unit 711 specifies the transformation position (X, Y, Z) in a fourth coordinate system from the pixel position (x, y, z) in a third coordinate system. The third coordinate system is a coordinate system having the origin at the upper left coordinate position in the three-dimensional OCT image. The third coordinate system is defined by the x coordinate axis having the B-scan direction as the x direction, a y coordinate axis, which is orthogonal to the x coordinate axis, having the C-scan direction as the y direction, and the z coordinate axis, which is orthogonal to both of the x coordinate axis and the y coordinate axis, having the A-scan direction as the z direction. The pixel position (x, y, z) in the OCT image is defined in the third coordinate system. The fourth coordinate system is defined by the Z coordinate axis, the X coordinate axis, and a Y coordinate axis. The Z coordinate axis has the traveling direction of the measurement light having the scan angle of 0 degrees with respect to the measurement optical axis passing through a predetermined site (for example, fovea) in the fundus Ef, as the Z direction. The X coordinate axis has the B-scan direction orthogonal to the Z coordinate axis at the predetermined site, as the X direction. The Y coordinate axis has the C-scan direction orthogonal to the Z coordinate axis at the predetermined site, as the Y direction. In the fourth coordinate system, a predetermined Z position is set as the origin of the Z coordinate axis so that the position of the scan radius r becomes the deepest portion in the measurement optical axis passing through the predetermined site (for example, the fovea). Further, a predetermined X position and Y position in the measurement optical axis passing through the predetermined site (for example, the fovea) are set as the origin of the X coordinate axis and the Y coordinate axis so as to have a predetermined depth direction length d as described below. The transformation position (X, Y, Z) is defined in the fourth coordinate system. The transformation position (X, Y, Z) corresponds to the pixel position (x, y, z), and is a position along the traveling direction of the measurement light passing through the scan center position Cs (A-scan direction).

The position specifying unit 711 can specify at least one of the X component, the Y component, and the Z component of the transformation position.

For the OCT image (tomographic image) in which the number of A-scan lines is "N" (N is a natural number) and the number of B-scan lines is "M" (M is a natural number), the transformation position (X, Y, Z), which corresponds to the pixel position (x, y, z) in the n-th (n is a natural number) A-scan line of the m-th (m is a natural number) B-scan line, is specified as shown in Equations (6) to (8).

[Equation 6]

$$X = \frac{w}{2} + \frac{(r - d + z) \times \tan\left(\frac{\varphi}{N} \times n - \frac{\varphi}{2}\right)}{\sqrt{\tan^2\left(\frac{\varphi}{N} \times n - \frac{\varphi}{2}\right) + \tan^2\left(\frac{\theta}{M} \times m - \frac{\theta}{2}\right) + 1}} \quad (6)$$

[Equation 7]

$$Y = \frac{lc}{2} + \frac{(r - d + z) \times \tan\left(\frac{\theta}{M} \times m - \frac{\theta}{2}\right)}{\sqrt{\tan^2\left(\frac{\varphi}{N} \times n - \frac{\varphi}{2}\right) + \tan^2\left(\frac{\theta}{M} \times m - \frac{\theta}{2}\right) + 1}} \quad (7)$$

[Equation 8]

$$Z = \frac{(r - d + z)}{\sqrt{\tan^2\left(\frac{\varphi}{N} \times n - \frac{\varphi}{2}\right) + \tan^2\left(\frac{\theta}{M} \times m - \frac{\theta}{2}\right) + 1}} - (r - h) \quad (8)$$

Here, the x component and the y component of the pixel position are expressed by Equations (9) to (13) from the length h in the depth direction, the length w in the B-scan direction, and the length is in the C-scan direction of the three-dimensional OCT image.

[Equation 9]
$$h = r - (r-d) \times \cos\frac{\varphi}{2} \quad (9)$$

[Equation 10]
$$w = 2r \times \sin\frac{\varphi}{2} \quad (10)$$

[Equation 11]
$$lc = 2r \times \sin\frac{\theta}{2} \quad (11)$$

[Equation 12]
$$x = n \quad (12)$$

[Equation 13]
$$y = m \quad (13)$$

In Equations (6) to (8), the x coordinate and the y coordinate of the pixel position are expressed by Equations (12) and Equation (13). Thus, the position specifying unit 711 can specify the transformation position (X, Y, Z) from the pixel position (x, y, z), based on the scan radius r, the scan angle φ, and the depth range d.

In some embodiments, for the scan data, the position specifying unit 711 can specify the transformation position (X, Y, Z), in the same way as above.

The position transforming unit 712 according to the present modification example transforms the pixel position (x, y, z) in the OCT image into the transformation position (X, Y, Z) specified by the position specifying unit 711. In some embodiments, for each of all pixel positions in the OCT image, the position specifying unit 711 specifies the transformation position and the position transforming unit 712 transforms the pixel position into the transformation position.

In the embodiments described above, the case where the tomographic image is corrected in the ophthalmologic apparatus including optical system 2, and the like has been described. However, the configuration according to the embodiments is not limited thereto. For example, the ophthalmologic information processing apparatus, which realizes the function of the data processor 7 shown in FIG. 6, may correct the tomographic image for the acquired OCT image (or the scan data), as described above, and may perform rotation processing on the corrected tomographic image based on the eccentricity amount and the eccentricity direction. In this case, the OCT image (or the scan data) is acquired by an external OCT apparatus (ophthalmologic apparatus).

In some embodiments, a program for causing a computer to execute the ophthalmologic information processing method described above is provided. Such a program can be stored in any computer-readable recording medium (for example, a non-transitory computer readable medium). Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

[Effects]

Hereinafter, the ophthalmologic information processing apparatus, the ophthalmologic apparatus, the ophthalmologic information processing method, and the program according to the embodiments will be described.

An ophthalmologic information processing apparatus (for example, apparatus including the data processor 7) analyzes an image (OCT image) of a subject's eye (E) formed by arranging a plurality of A-scan images acquired by performing OCT scan on inside the subject's eye with measurement light deflected around a scan center position (Cs). The ophthalmologic information processing apparatus includes a correcting unit (shape correcting unit 71), a region specifying unit (layer region specifying unit 721), and a direction specifying unit (normal direction specifying unit 722). The correcting unit is configured to transform a pixel position in the image into a transformation position along a traveling direction of the measurement light passing through the scan center position. The region specifying unit is configured to specify a predetermined layer region by analyzing the image in which the pixel position has been transformed by the correcting unit. The direction specifying unit is configured to specify a normal direction of the layer region specified by the region specifying unit.

According to such a configuration, the image is corrected by transforming the pixel positions of the image of the subject's eye into the transformation positions along the traveling direction of the measurement light passing through the scan center position, and the normal direction of the predetermined layer region in the corrected image is specified. This allows to accurately grasp the morphology of the fundus of the subject's eye, or the like, for the peripheral part of the fundus or when the shape of the fundus is deformed.

In some embodiments, the region specifying unit includes a boundary specifying unit (721A) configured to specify a boundary line of the layer region; and an approximate processor (721B) configured to obtain an approximate curve of the boundary line specified by the boundary specifying unit, and the direction specifying unit is configured to specify the normal direction at a position on the approximate curve obtained by the approximate processor.

According to such a configuration, the morphology of the peripheral part of the fundus or the fundus whose shape is deformed can be accurately grasped using the two-dimensional image of the subject's eye.

In some embodiments, the region specifying unit includes a boundary specifying unit (721A) configured to specify a boundary surface of the layer region; and an approximate processor (721B) configured to obtain an approximate curved surface of the boundary surface specified by the boundary specifying unit, and the direction specifying unit is configured to specify the normal direction at a position on the approximate curved surface obtained by the approximate processor.

According to such a configuration, the morphology of the peripheral part of the fundus or the fundus whose shape is deformed can be accurately grasped using the three-dimensional image of the subject's eye.

Some embodiments further include a calculator (layer thickness calculator 723) configured to obtain a distance in the normal direction in the layer region specified by the region specifying unit.

According to such a configuration, a thickness of the layer region in the peripheral part of the fundus or a thickness of the layer region when the shape of the fundus is deformed can be accurately acquired, similar to the central part of the fundus.

Some embodiments further include a distribution information generator (724) configured to generate distribution information representing a distribution of the distance calculated by the calculator.

According to such a configuration, a distribution of the thickness of the layer region in the peripheral part of the fundus or a distribution of the thickness of the layer region when the shape of the fundus is deformed can be accurately acquired, similar to the central part of the fundus.

Some embodiments include a display controller (51A) configured to display an image corresponding to the distribution information on a display means (display device in the UI unit 8) in a display mode according to the distance.

According to such a configuration, a distribution of the thickness of the layer region in the peripheral part of the fundus or a distribution of the thickness of the layer region when the shape of the fundus is deformed can be accurately grasped, similar to the central part of the fundus.

In some embodiments, the display controller is configured to superimpose the image corresponding to the distribution information on the image in which the pixel position has been transformed by the correcting unit, and to display the superimposed image on the display means.

According to such a configuration, a distribution of the thickness of the layer region in the peripheral part of the fundus or a distribution of the thickness of the layer region when the shape of the fundus is deformed can be accurately grasp, similar to the central part of the fundus, by associating an image corresponding to the distribution information with an image whose shape of the fundus or the like has been corrected.

In some embodiments, the display controller is configured to superimpose the image corresponding to the distribution information on a result of a kinetic perimetry or a static perimetry of the subject's eye, and to display the superimposed image on the display means.

According to such a configuration, a distribution of the thickness of the layer region in the peripheral part of the fundus or a distribution of the thickness of the layer region when the shape of the fundus is deformed can be accurately grasped, similar to the central part of the fundus, in relation to the result of the perimetry of the subject's eye.

In some embodiments, the display controller is configured to display an image, in which the pixel position has been transformed by the correcting unit, in the normal direction.

According to such a configuration, an image in which the morphology of the fundus and the like is depicted according to the actual shape of the subject's eye can be displayed.

Some embodiments include a display controller (51A) configured to display the image, in which the pixel position has been transformed by the correcting unit, in the normal direction.

According to such a configuration, an image in which the morphology of the fundus and the like is depicted according to the actual shape of the subject's eye can be displayed.

An ophthalmologic apparatus (1) according to some embodiments includes an OCT unit (interference optical system 40, scan optical system 30, and image forming unit 6 (or data processor 7)) configured to acquire a tomographic image of the subject's eye using optical coherence tomography: and the ophthalmologic information processing apparatus described above.

According to such a configuration, the ophthalmologic apparatus capable of accurately grasping the morphology of the fundus or the like of the subject's eye can be provided, for the peripheral part of the fundus or when the shape of the fundus is deformed.

An ophthalmologic information processing method according to some embodiments analyzes an image of a subject's eye (E) formed by arranging a plurality of A-scan images acquired by scanning inside the subject's eye with measurement light deflected around a scan center position (Cs). The ophthalmologic information processing method includes a correcting step of transforming a pixel position in the image into a transformation position along a traveling direction of the measurement light passing through the scan center position; a region specifying step of specifying a predetermined layer region by analyzing the image in which the pixel position has been transformed in the correcting step, and a direction specifying step of specifying a normal direction of the layer region specified in the region specifying step.

According to such a method, the image is corrected by transforming the pixel positions of the image of the subject's eye into the transformation positions along the traveling direction of the measurement light passing through the scan center position, and the normal direction of the predetermined layer region in the corrected image is specified. This allows to accurately grasp the morphology of the fundus of the subject's eye, or the like, for the peripheral part of the fundus or when the shape of the fundus is deformed.

Some embodiments include a calculating step of obtaining a distance in the normal direction in the layer region specified in the region specifying step.

According to such a method, a thickness of the layer region in the peripheral part of the fundus or a thickness of the layer region when the shape of the fundus is deformed can be accurately acquired, similar to the central part of the fundus.

Some embodiments include a display control step of displaying an image corresponding to distribution information representing a distribution of the distance on a display means (display device in the UI unit 8) in a display mode according to the distance.

According to such a method, a distribution of the thickness of the layer region in the peripheral part of the fundus or a distribution of the thickness of the layer region when the shape of the fundus is deformed can be accurately grasped, similar to the central part of the fundus.

In some embodiments, the display control step is performed to superimpose the image corresponding to the distribution information on the image in which the pixel position has been transformed in the correcting step, and to display the superimposed image on the display means.

According to such a method, a distribution of the thickness of the layer region in the peripheral part of the fundus or a distribution of the thickness of the layer region when the shape of the fundus is deformed can be accurately grasp, similar to the central part of the fundus, by associating an image corresponding to the distribution information with an image whose shape of the fundus or the like has been corrected.

In some embodiments, the display control step is performed to superimpose the image corresponding to the distribution information on a result of a kinetic perimetry or a static perimetry of the subject's eye, and to display the superimposed image on the display means.

According to such a method, a distribution of the thickness of the layer region in the peripheral part of the fundus or a distribution of the thickness of the layer region when the shape of the fundus is deformed can be accurately grasped, similar to the central part of the fundus, in relation to the result of the perimetry of the subject's eye.

Some embodiments include a display control step of displaying an image, in which the pixel position has been transformed by the correcting unit, in the normal direction.

According to such a method, an image in which the morphology of the fundus and the like is depicted according to the actual shape of the subject's eye can be displayed.

A program according to some embodiments causes a computer to execute each step of the ophthalmologic information processing method of any one of described above.

According to such a program, the image is corrected by transforming the pixel positions of the image of the subject's eye into the transformation positions along the traveling direction of the measurement light passing through the scan center position, and the normal direction of the predetermined layer region in the corrected image is specified. This allows to accurately grasp the morphology of the fundus of the subject's eye, or the like, for the peripheral part of the fundus or when the shape of the fundus is deformed.

<Others>

The above-described some embodiments or the modification examples thereof are merely examples for carrying out the present invention. Those who intend to implement the present invention can apply any modification, omission, addition, or the like within the scope of the gist of the present invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus for analyzing an image of a subject's eye formed by arranging a plurality of A-scan images acquired by performing an Optical Coherence Tomography (OCT) scan on an inside the subject's eye with measurement light deflected around a scan center position, the ophthalmologic information processing apparatus comprising processing circuitry configured to:

transform pixel positions in the image into transformation positions along traveling directions of the measurement light passing through the scan center position by transforming pixel positions in each A-scan image into transformation positions along the traveling directions of the measurement light used to form the A-scan image;

specify a layer region by analyzing the image in which the pixel position has been transformed; and specify a normal direction of the layer region.

2. The ophthalmologic information processing apparatus of claim 1, wherein the processing circuitry is further configured to:

specify a boundary line of the layer region;
obtain an approximate curve of the boundary line; and
specify the normal direction at a position on the approximate curve.

3. The ophthalmologic information processing apparatus of claim 1, wherein the processing circuitry is further configured to:

specify a boundary surface of the layer region; and
obtain an approximate curved surface of the boundary surface; and
specify the normal direction at a position on the approximate curved surface.

4. The ophthalmologic information processing apparatus of claim 1, wherein the processing circuitry is further configured to:

obtain a distance in the normal direction in the layer region.

5. The ophthalmologic information processing apparatus of claim 4, wherein the processing circuitry is further configured to:

generate distribution information representing a distribution of the distance in the normal direction in the layer region.

6. The ophthalmologic information processing apparatus of claim 5, further comprising:

a display controller configured to display a distribution information image corresponding to the distribution information on a display in a display mode according to the distance.

7. The ophthalmologic information processing apparatus of claim 6, wherein the display controller is configured to superimpose the distribution information image corresponding to the distribution information on the image in which the pixel position has been transformed, and to display the superimposed image on the display.

8. The ophthalmologic information processing apparatus of claim 6, wherein the display controller is configured to superimpose the distribution information image corresponding to the distribution information on a result of a kinetic perimetry or a static perimetry of the subject's eye, and to display the superimposed image on the display.

9. The ophthalmologic information processing apparatus of claim 6, wherein the display controller is configured to display an image in which the pixel position has been transformed in the normal direction.

10. The ophthalmologic information processing apparatus of claim 1, further comprising:

a display controller configured to display an image in which the pixel position has been transformed in the normal direction.

11. An ophthalmologic apparatus, comprising:

an Optical Coherence Tomography (OCT) scanner configured to acquire a tomographic image of a subject's eye using optical coherence tomography; and an ophthalmologic information processing apparatus for analyzing the tomographic image of the subject's eye formed by arranging a plurality of A-scan images acquired by performing an OCT scan on an inside the subject's eye with measurement light deflected around a scan center position, the ophthalmologic information processing apparatus including processing circuitry configured to transform pixel positions in the image into transformation positions along traveling directions of the measurement light passing through the scan center position by transforming pixel positions in each A-scan image into transformation positions along the traveling directions of the measurement light used to form the A-scan image,
specify a layer region by analyzing the image in which the pixel position has been transformed, and
specify a normal direction of the layer region.

12. An ophthalmologic information processing method for analyzing an image of a subject's eye formed by arranging a plurality of A-scan images acquired by performing an Optical Coherence Tomography (OCT) scan on an inside the subject's eye with measurement light deflected around a scan center position, the ophthalmologic information processing method comprising:
transforming pixel positions in the image into transformation positions along traveling directions of the measurement light passing through the scan center position by transforming pixel positions in each A-scan image into transformation positions along the traveling directions of the measurement light used to form the A-scan image;
specifying a layer region by analyzing the image in which the pixel position has been transformed; and
specifying a normal direction of the layer region.

13. The ophthalmologic information processing method of claim 12, further comprising:
obtaining a distance in the normal direction in the layer region.

14. The ophthalmologic information processing method of claim 13, further comprising:
displaying a distribution information image corresponding to distribution information representing a distribution of the distance on a display in a display mode according to the distance in the normal direction in the layer region.

15. The ophthalmologic information processing method of claim 14, wherein
the displaying includes superimposing the distribution information image corresponding to the distribution information on the image in which the pixel position has been transformed and displaying the superimposed image on the display.

16. The ophthalmologic information processing method of claim 14, wherein
the displaying includes superimposing the distribution information image corresponding to the distribution information on a result of a kinetic perimetry or a static perimetry of the subject's eye, and displaying the superimposed image on the display.

17. The ophthalmologic information processing method of claim 12, further comprising:
displaying an image in which the pixel position has been transformed in the normal direction.

18. A non-transitory computer readable recording medium storing a program of causing a computer to execute an ophthalmologic information processing method for analyzing an image of a subject's eye formed by arranging a plurality of A-scan images acquired by performing an Optical Coherence Tomography (OCT) scan on an inside the subject's eye with measurement light deflected around a scan center position, the ophthalmologic information processing method comprising:
transforming pixel positions in the image into transformation positions along traveling directions of the measurement light passing through the scan center position by transforming pixel positions in each A-scan image into transformation positions along the traveling directions of the measurement light used to form the A-scan image;
specifying a layer region by analyzing the image in which the pixel position has been transformed; and
specifying a normal direction of the layer region.

* * * * *